US011756668B2

(12) United States Patent
Talmor et al.

(10) Patent No.: US 11,756,668 B2
(45) Date of Patent: Sep. 12, 2023

(54) SYSTEMS METHODS DEVICES CIRCUITS AND COMPUTER EXECUTABLE CODE FOR TRACKING EVALUATING AND FACILITATING A MEDICAL PROCEDURE

(71) Applicant: ALEPH BOT LTD., Atlit (IL)

(72) Inventors: Ofer Talmor, Atlit (IL); Chen Itzhaki, Herzeliya (IL)

(73) Assignee: ALEPH BOT LTD, Atlit (IL)

( * ) Notice: Subject to any disclaimer, the term of this patent is extended or adjusted under 35 U.S.C. 154(b) by 300 days.

(21) Appl. No.: 16/763,329

(22) PCT Filed: Nov. 12, 2018

(86) PCT No.: PCT/IB2018/058880
§ 371 (c)(1),
(2) Date: May 12, 2020

(87) PCT Pub. No.: WO2019/111077
PCT Pub. Date: Jun. 13, 2019

(65) Prior Publication Data
US 2020/0335208 A1    Oct. 22, 2020

Related U.S. Application Data

(60) Provisional application No. 62/584,834, filed on Nov. 12, 2017.

(51) Int. Cl.
*G16H 20/40*    (2018.01)
*G06N 3/08*    (2023.01)
(Continued)

(52) U.S. Cl.
CPC .............. *G16H 20/40* (2018.01); *G06N 3/08* (2013.01); *G06V 10/764* (2022.01);
(Continued)

(58) Field of Classification Search
None
See application file for complete search history.

(56) References Cited

U.S. PATENT DOCUMENTS 9,788,907 B1\* 10/2017 Alvi ..................... H04L 67/2804
2008/0269596 A1\* 10/2008 Revie ..................... A61B 90/39
705/28

(Continued)

*Primary Examiner* — Hung Q Dang
(74) *Attorney, Agent, or Firm* — Vladimir Sherman; PROFESSIONAL PATENT SOLUTIONS LTD

(57) ABSTRACT

Disclosed is a system for medical procedure tracking, evaluation and assistance, wherein one or more video cameras, one or more acoustic sensors or one or more medical device interfaces acquire video, audio or medical device feeds from a medical treatment setting. A scene evaluation module detects scene related features in the video, audio or medical device feeds. A procedure compliance assessment module compares one or more scene related features detected and reported by the scene evaluation module to a list of expected actions or equipment usages associated with the procedure being performed in the treatment setting. A procedure assistance module provides compliance based procedure related action recommendations or instructions from within the list of expected actions or equipment usages.

11 Claims, 31 Drawing Sheets

(51) Int. Cl.
| | |
|---|---|
| *G06V 10/764* | (2022.01) |
| *G06V 10/80* | (2022.01) |
| *G06V 10/82* | (2022.01) |
| *G06V 20/40* | (2022.01) |
| *G06V 20/52* | (2022.01) |
| *G16H 40/20* | (2018.01) |
| *G16H 40/60* | (2018.01) |
| *G06F 18/2413* | (2023.01) |
| *G06F 18/25* | (2023.01) |
| *G06N 5/045* | (2023.01) |
| *G06N 20/00* | (2019.01) |
| *G16H 40/63* | (2018.01) |
| *G16H 40/67* | (2018.01) |

(52) U.S. Cl.
CPC ............ *G06V 10/803* (2022.01); *G06V 10/82* (2022.01); *G06V 20/41* (2022.01); *G06V 20/46* (2022.01); *G06V 20/52* (2022.01); *G16H 40/20* (2018.01); *G16H 40/60* (2018.01)

(56) References Cited

U.S. PATENT DOCUMENTS

| | | | |
|---|---|---|---|
| 2013/0113929 A1* | 5/2013 | DeLand | G06V 20/52 |
| | | | 382/103 |
| 2015/0100066 A1* | 4/2015 | Kostrzewski | A61B 90/06 |
| | | | 606/130 |
| 2016/0381256 A1* | 12/2016 | Aguirre-Valencia | ........ |
| | | | H04N 13/30 |
| | | | 348/46 |
| 2017/0337682 A1* | 11/2017 | Liao | G06T 7/0012 |
| 2018/0153632 A1* | 6/2018 | Tokarchuk | B25J 9/1689 |
| 2018/0168755 A1* | 6/2018 | Cagle | A61B 34/74 |

* cited by examiner

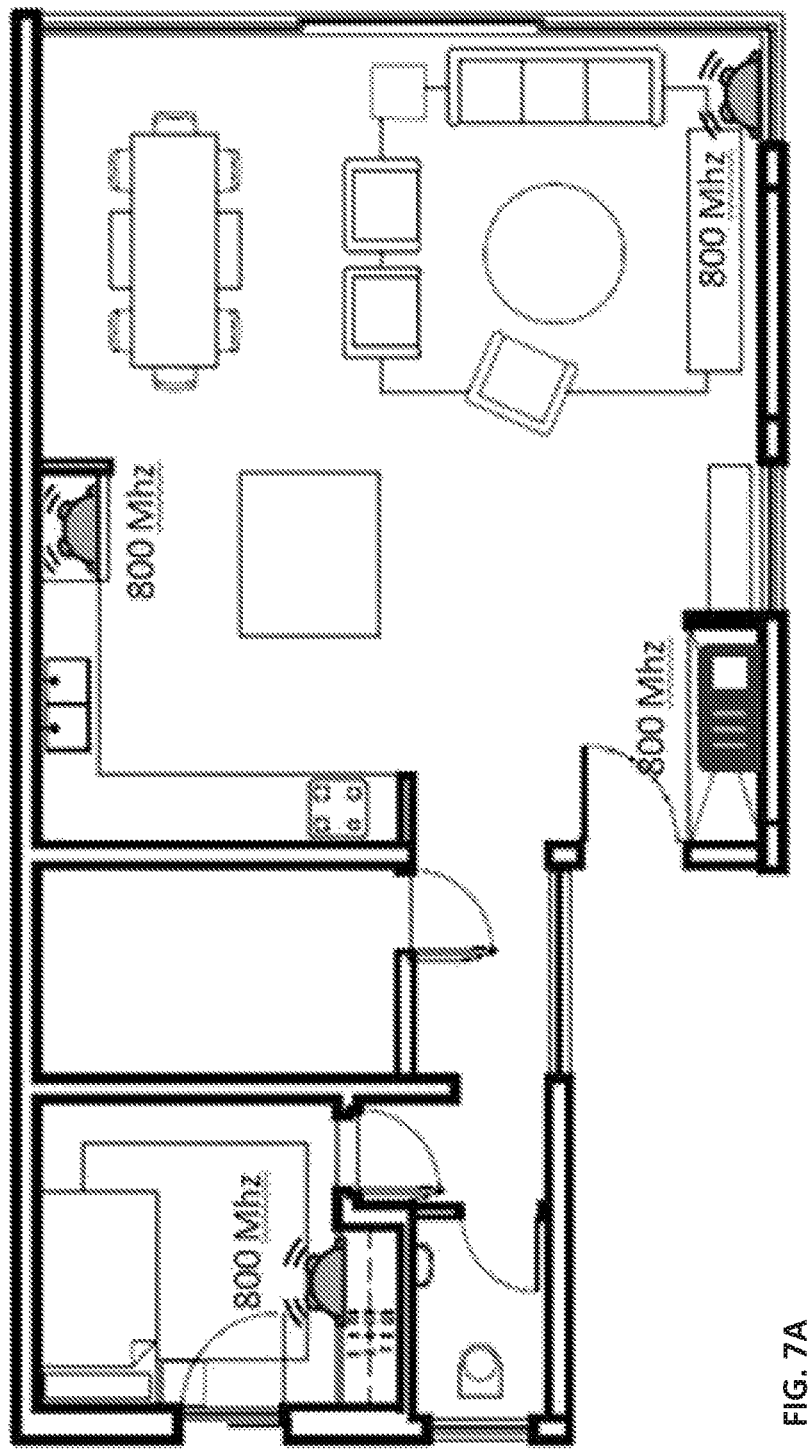

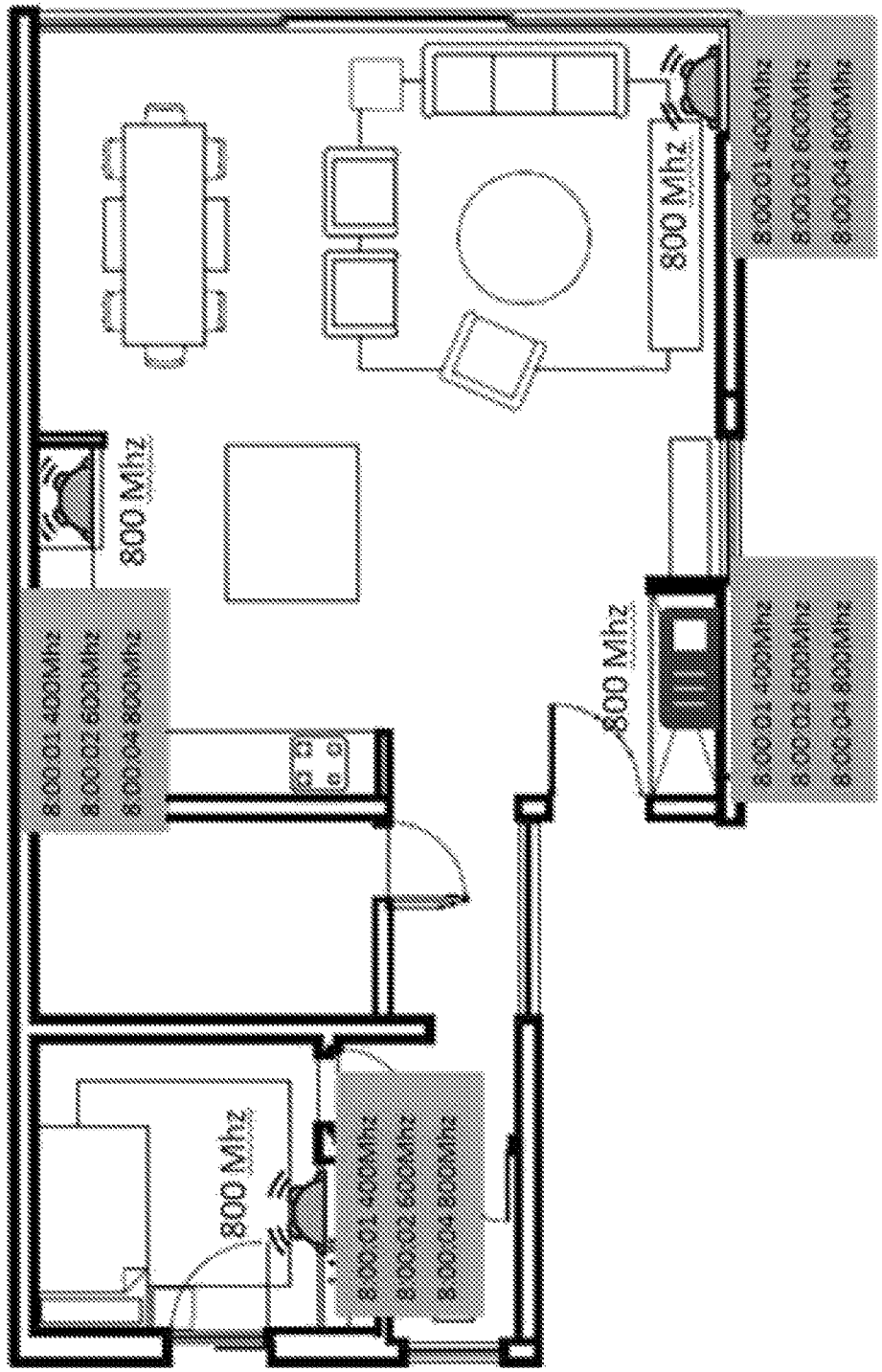
FIG. 7C  Step 3: The plan is being distributed to the different beacons.

Step 4: At the designated time, all beacons change their frequency to 400Mhz concurrently.

SYSTEMS METHODS DEVICES CIRCUITS AND COMPUTER EXECUTABLE CODE FOR TRACKING EVALUATING AND FACILITATING A MEDICAL PROCEDURE

RELATED APPLICATIONS SECTION

The present application claims priority from applicant's U.S. Provisional Patent Application No. 62/584,834; U.S. Provisional Patent Application No. 62/593,933; U.S. Provisional Patent Application No. 62/607,923; and U.S. Provisional Patent Application No. 62/618,638. All of which applications are hereby incorporated by reference in their entirety.

FIELD OF THE INVENTION

The present invention generally relates to the fields of medical procedure monitoring, documentation and decision support. More specifically, the present invention relates to systems, methods, devices, circuits and functionally associated computer executable code for tracking, evaluating and facilitating a medical procedure.

BACKGROUND

Medical procedures, especially emergency procedures are performed under pressure, where time is a critical factor. The medical staff in these kinds of procedures, usually faces a long list of tasks and decisions. Many of the involved tasks may not be performed in parallel, including, for example: treating the patient, the documentation of the procedure flow, following the exact steps in the medical scheme and/or receiving data about the patient from various resources simultaneously. Mistakes in any of these steps could be critical. Furthermore, providing proper documentation of the procedure sometimes requires an additional role of a medical scribe, whereas in other procedures, medical staff members involved in the procedure (e.g., physician, physician assistance, surgeon, anesthesiologist, paramedic, nurse) will need to perform the required documentation.

There remains a need, in the fields of Medical Procedure monitoring, documentation and decision support, for systems, methods, devices, circuits and computer executable code, for monitoring a medical procedure, providing procedure related notifications and decision support, optionally in real-time, to the medical staff participating in the procedure and documenting it for future reference.

SUMMARY OF THE INVENTION

The present invention, includes a computerized medical procedure facilitation system, wherein electric and/or digital outputs from one or more sensors and/or from one or more medical devices, or other devices, monitoring the medical procedure, are utilized to collect procedure associated data. The collected data may be analyzed to identify the monitored medical procedure, specific steps thereof being executed and/or patient medical parameters associated therewith.

The analysis results may be documented/logged at least partially in respect of: the identified procedure, the identified procedure step and/or information about the specific patient on which the procedure is being carried out. A decision support system may access and utilize the collected/documented/logged data to provide: subsequent procedure steps predictions, procedure/procedure-step related medical suggestions and/or procedure/procedure-step related auxiliary tools. The decision support system may at least partially consider medical data/records associated with the specific patient on which the procedure is being carried out, wherein the medical data/records of the patient may be based on the collected/documented/logged analysis results and/or combined with patient related data from other sources.

A system in accordance with some embodiments of the present invention, may include any combination of the components described herein. In some embodiments, these components may be packed together to a unified device or apparatus, optionally as a standalone device; in some embodiments, at least some of these components may be deployed on: a cart, a bed, or any other equipment or object in the environment of the medical procedure; and/or, in some embodiments, at least some of the system components may be at a location other than the environment of the medical procedure—while being functionally-associated/communicatively-networked with system components in it. At least some of the system components may include computerized, electronic and/or digital elements and may implement respective capabilities and functions.

An exemplary system, in accordance with some embodiments of the present invention, may include methods, circuits, devices, systems and functionally associated computer executable code for visually, acoustically and/or medically (i.e. using medical device outputs) tracking, evaluating and facilitating a medical treatment procedure. According to some embodiments there may be provided a medical procedure tracking and assistance system configured to perform procedure execution inspection and/or validation and to provide, optionally in real-time, instructional, operational and/or informational support based thereof.

A system according to embodiments of the present invention may for example include a procedure setting data acquisition module, having one or more, or any number of, video cameras (or any image sensors—optical-sensors/camera/video, x-ray/penetrating-wave/CT, MRI, thermography), one or more, or any number of, acoustic sensors and/or one or more medical device interfaces, within a treatment setting, such as for example an emergency room.

Video feeds from the camera(s), audio feeds from the audio sensors and/or medical device outputs, may be provided to a scene/setting evaluation module which may include signal processing circuits and algorithms—optionally including and utilizing artificial intelligence, machine learning and deep learning models and methodologies—to detect scene related features, including performed actions and medical equipment usage[specific actions, specific medical equipment usage, specific medical tools usage and/or specific chemicals/medicines/drugs usage], from the specific treatment setting covered by the cameras and audio sensors, the medical devices monitoring the treated patient and/or retrieved medical records of the patient.

A procedure compliance assessment module may compare one or more scene related features detected and reported by the scene/setting evaluation module to a list of expected actions or equipment usages associated with a procedure to be performed in the treatment scene/setting and/or with specific parts, stages or steps of the procedure.

A procedure assistance module, based on the results of the comparison of the setting features to the expected actions and usages associated with the procedure, may generate and provide suggestions and recommendations to medical staff members participating in the procedure and/or commands to medical devices utilized as part of the procedure. The procedure assistance module may further generate documentation of the procedure and create or update related medical database records. A grade or score, representing the performance of medical staff members participating in the procedure, or specific stages thereof, may be likewise generated.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings:

FIG. 7A is a schematic drawing of an exemplary system/module for radio frequency (RF) based object localization, in accordance with some embodiments of the present invention;

FIG. 7C is a schematic drawing of an exemplary system/module for radio frequency (RF) based object localization, in accordance with some embodiments of the present invention;

Figure 1:
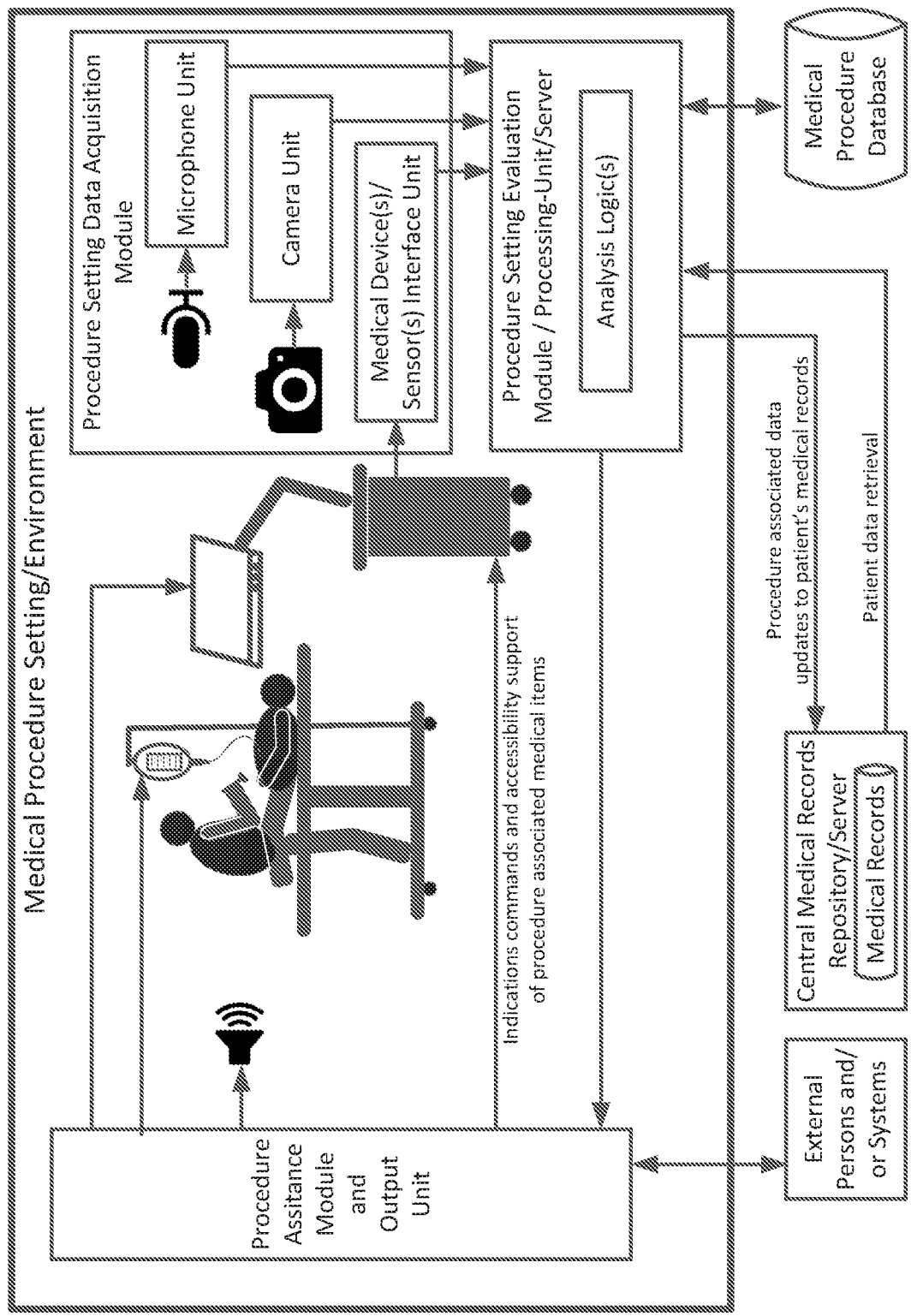
FIG. 1 is a schematic drawing of an exemplary system for tracking, evaluating and facilitating medical procedures, in accordance with some embodiments.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

In the following detailed description, numerous specific details are set forth in order to provide a thorough understanding of some embodiments. However, it will be understood by persons of ordinary skill in the art that some embodiments may be practiced without these specific details. In other instances, well-known methods, procedures, components, units and/or circuits have not been described in detail so as not to obscure the discussion.

Functions, operations, components and/or features described herein with reference to one or more embodiments, may be combined with, or may be utilized in combination with, one or more other functions, operations, components and/or features described herein with reference to one or more other embodiments, or vice versa.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "includes", "including", "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

The present disclosure is to be considered as an exemplification of the invention, and is not intended to limit the invention to the specific embodiments illustrated by the figures or description below.

Unless specifically stated otherwise, as apparent from the following discussions, it is appreciated that throughout the specification discussions utilizing terms such as "processing", "computing", "calculating", "determining", or the like, may refer to the action and/or processes of a computer, computing system, computerized mobile device, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

In addition, throughout the specification discussions utilizing terms such as "storing", "hosting", "caching", "saving", or the like, may refer to the action and/or processes of 'writing' and 'keeping' digital information on a computer or computing system, or similar electronic computing device, and may be interchangeably used. The term "plurality" may be used throughout the specification to describe two or more components, devices, elements, parameters and the like.

Some embodiments of the invention, for example, may take the form of an entirely hardware embodiment, an entirely software embodiment, or an embodiment including both hardware and software elements. Some embodiments may be implemented in software, which includes but is not limited to firmware, resident software, microcode, or the like.

Furthermore, some embodiments of the invention may take the form of a computer program product accessible from a computer-usable or computer-readable medium providing program code for use by or in connection with a computer or any instruction execution system. For example, a computer-usable or computer-readable medium may be or may include any apparatus that can contain, store, communicate, propagate, or transport the program for use by or in connection with the instruction execution system, apparatus, or device, for example a computerized device running a web-browser.

In some embodiments, the medium may be an electronic, magnetic, optical, electromagnetic, infrared, or semiconductor system (or apparatus or device) or a propagation medium. Some demonstrative examples of a computer-readable medium may include a semiconductor or solid state memory, magnetic tape, a removable computer diskette, a random access memory (RAM), a read-only memory (ROM), a rigid magnetic disk, and an optical disk. Some demonstrative examples of optical disks include compact disk-read only memory (CD-ROM), compact disk-read/write (CD-R/W), and DVD.

In some embodiments, a data processing system suitable for storing and/or executing program code may include at least one processor coupled directly or indirectly to memory elements, for example, through a system bus. The memory elements may include, for example, local memory employed during actual execution of the program code, bulk storage, and cache memories which may provide temporary storage of at least some program code in order to reduce the number of times code must be retrieved from bulk storage during execution. The memory elements may, for example, at least partially include memory/registration elements on the user device itself.

In some embodiments, input/output or I/O devices (including but not limited to keyboards, displays, pointing devices, etc.) may be coupled to the system either directly or through intervening I/O controllers. In some embodiments, network adapters may be coupled to the system to enable the data processing system to become coupled to other data processing systems or remote printers or storage devices, for example, through intervening private or public networks. In some embodiments, modems, cable modems and Ethernet cards are demonstrative examples of types of network adapters. Other suitable components may be used.

Lastly, throughout the specification, discussions utilizing terms such as "setting", "environment", "scene", or the like, may refer to the place and/or vicinity of a location where a medical process, procedure, treatment or examination is being performed and may be used interchangeably. The solutions, techniques, systems, devices, components and methods in the specification and accompanying drawings are described in the context of a medical procedure, this however, is not to limit in any way the teachings herein to medical applications or medical context—all or some of which teachings may be likewise applicable to other fields, contexts and/or scenarios.

SUMMARY

The present invention, includes a computerized medical procedure facilitation system, wherein electric and/or digital outputs from one or more sensors and/or from one or more medical devices, or other devices, monitoring the medical procedure, are utilized to collect procedure associated data. The collected data may be analyzed to identify the monitored medical procedure, specific steps thereof being executed and/or patient medical parameters associated therewith.

The analysis results may be documented/logged at least partially in respect of: the identified procedure, the identified procedure step and/or information about the specific patient on which the procedure is being carried out. A decision support system may access and utilize the collected/documented/logged data to provide: subsequent procedure steps predictions, procedure/procedure-step related medical suggestions and/or procedure/procedure-step related auxiliary tools. The decision support system may at least partially consider medical data/records associated with the specific patient on which the procedure is being carried out, wherein the medical data/records of the patient may be based on the collected/documented/logged analysis results and/or combined with patient related data from other sources.

A system in accordance with some embodiments of the present invention, may include any combination of the components described herein. In some embodiments, these components may be packed together to a unified device or apparatus, optionally as a standalone device; in some embodiments, at least some of these components may be deployed on: a cart, a bed, or any other equipment or object in the environment of the medical procedure; and/or, in some embodiments, at least some of the system components may be at a location other than the environment of the medical procedure—while being functionally-associated/communicatively-networked with system components in it. At least some of the system components may include computerized, electronic and/or digital elements and may implement respective capabilities and functions. The computerized, electronic and/or digital elements may be implemented on a single computerized device, unit, server or platform; or, may be implemented, at least partially, as a distributed computer platform including multiple computerized devices, units or servers, functionally and/or communicatively associated with one another.

An exemplary system, in accordance with some embodiments of the present invention, may include methods, circuits, devices, systems and functionally associated computer executable code for visually, acoustically and/or medically (i.e. using medical device outputs) tracking, evaluating and facilitating a medical treatment procedure. According to some embodiments there may be provided a medical procedure tracking and assistance system configured to perform procedure execution inspection and/or validation and to provide, optionally in real-time, instructional, operational and/or informational support based thereof.

A system according to embodiments of the present invention may for example include a procedure setting data acquisition module, having one or more, or any number of, video cameras (or image sensors—e.g. optical-sensors/camera/video, x-ray/penetrating-wave/CT, MRI, thermography), one or more, or any number of, acoustic sensors and/or one or more, or any number of, medical device interfaces, within a treatment setting, such as for example an emergency room.

Video feeds from the camera(s), audio feeds from the audio sensors and/or medical device outputs, may be provided to a scene/setting evaluation module which may include signal processing circuits and algorithms—optionally including and utilizing artificial intelligence, machine learning and deep learning models and methodologies—to detect scene related features, including performed actions and medical equipment usage (e.g. specific actions, specific medical equipment usage, specific medical tools usage and/or specific chemicals/medicines/drugs usage), from the specific treatment setting covered by the cameras and audio sensors, the medical devices monitoring the treated patient and/or retrieved medical records of the patient.

A procedure compliance assessment module may compare one or more scene related features detected and reported by the scene/setting evaluation module to a list of expected actions or equipment usages associated with a procedure to be performed in the treatment scene/setting and/or with specific parts, stages or steps of the procedure.

A procedure assistance module, based on the results of the comparison of the setting features to the expected actions and usages associated with the procedure, may generate and provide suggestions and recommendations to medical staff members participating in the procedure and/or commands to medical devices utilized as part of the procedure. The procedure assistance module may further generate documentation of the procedure and create or update related medical database records. A grade or score, representing the performance of medical staff members participating in the procedure, or specific stages thereof, may be likewise generated.

A system in accordance with some embodiments of the present invention, may include a processing module comprising one or more processing logics—adapted for specific processing tasks executed by the system and/or for performing a combination of processing tasks—wherein the processing logic(s) may include any combination of: computer hardware components, electronic processing circuitries, and/or computer executable code.

Processing tasks executed by the system's processing module may, for example, include: processing of signals and raw data feeds acquired by the procedure data acquisition module; processing related to the analysis tasks of the medical procedure setting, by the procedure setting evaluation module; processing related to generation and relaying of recommendations, notifications, instructions, tools, commands and/or documentation tasks, made by the procedure assistance module; and/or any system and component management, or other, processing tasks performed by the system.

A system in accordance with some embodiments of the present invention, may include a communication module comprising one or more communication logics—adapted for specific communication and data transfer/receipt tasks executed by the system and/or for performing a combination of communication tasks—wherein the communication logic(s) may include any combination of: computer hardware components, electronic processing circuitries, and/or computer executable code.

Communication tasks executed by the system's communication module may, for example, include: receiving of signals and raw data feeds acquired by the procedure data acquisition module; relaying of medical procedure setting analysis results, generated by the procedure setting evaluation module; communicating recommendations, notifications, instructions, tools, commands and/or documentation tasks data, generated by the procedure assistance module to medical staff members and medical devices/equipment/systems; and/or any system and component, or other, communication tasks performed by the system.

According to some embodiments, some or all of the system's communication and processing modules/logics may be functionally associated with specific system modules, components and/or units—and designed to perform specific tasks related to their operation. According to some embodiments, the system's communication and processing modules/logics may be implemented at least partially in a centralized configuration, wherein one or more main processing/communication modules/logics are designed to perform processing/communication tasks based on requests received from multiple different system modules, components and/or units.

In FIG. 1, there is shown a schematic drawing of an exemplary system for tracking, evaluating and facilitating medical procedures, in accordance with some embodiments; the shown system includes: A microphone/sound-recording unit, a camera/imaging unit and a medical device/s and/or medical sensor/s interface unit—adapted for monitoring, optionally in parallel/concert, the medical procedure being carried out and its environment and for collecting information about it. Collected data and/or processed/pre-processed derivations thereof are relayed to the shown processing unit/server and analyzed by the shown analysis logic. The analysis logic may utilize any analysis tools, techniques or models as part of its operation, including, but not limited to, any combination of artificial intelligence and/or machine learning based analysis, known today or to be devised in the future; for example: neural networks, deep learning, support vector machines, statistical and distribution analysis, decision trees, association rules, inductive logic, clustering and/or others.

The exemplary processing and analysis of the data includes referencing a medical procedure database, identifying—based on the collected data—the process being carried out and its current stage(s), documenting the process and registering it to the database and optionally updating general procedure related records of the database with inputs from the current one.

The exemplary processing and analysis of the data further includes referencing a central medical records repository/server, retrieving medical data related to the subject (i.e. patient) of the medical procedure and optionally, updating the records of the medical records repository/server with procedure associated data, based on the results of the analysis.

The exemplary processing and analysis of the data further includes the generation/issuance of decision and knowledge support suggestions/notifications, to the medical staff carrying out the current medical procedure, wherein the suggestions/notification are at least partially based on related information in the database about the current procedure or a similar procedure. Suggestions/notifications are then relayed to an output unit for dispatching and outputting them to relevant medical staff members, for example through an acoustic and/or visual output means or devices (e.g. speaker, display) and/or through medical equipment components associated with the medical procedure. According to some embodiments, output may also be provided through a wearable or haptic device. The output unit shown is further adapted to notify, update or request further inputs—from persons (e.g. experts, researches, medical department mangers) or machines (e.g. patient medical records systems/databases, medicine inventory management systems).

Figure 2:
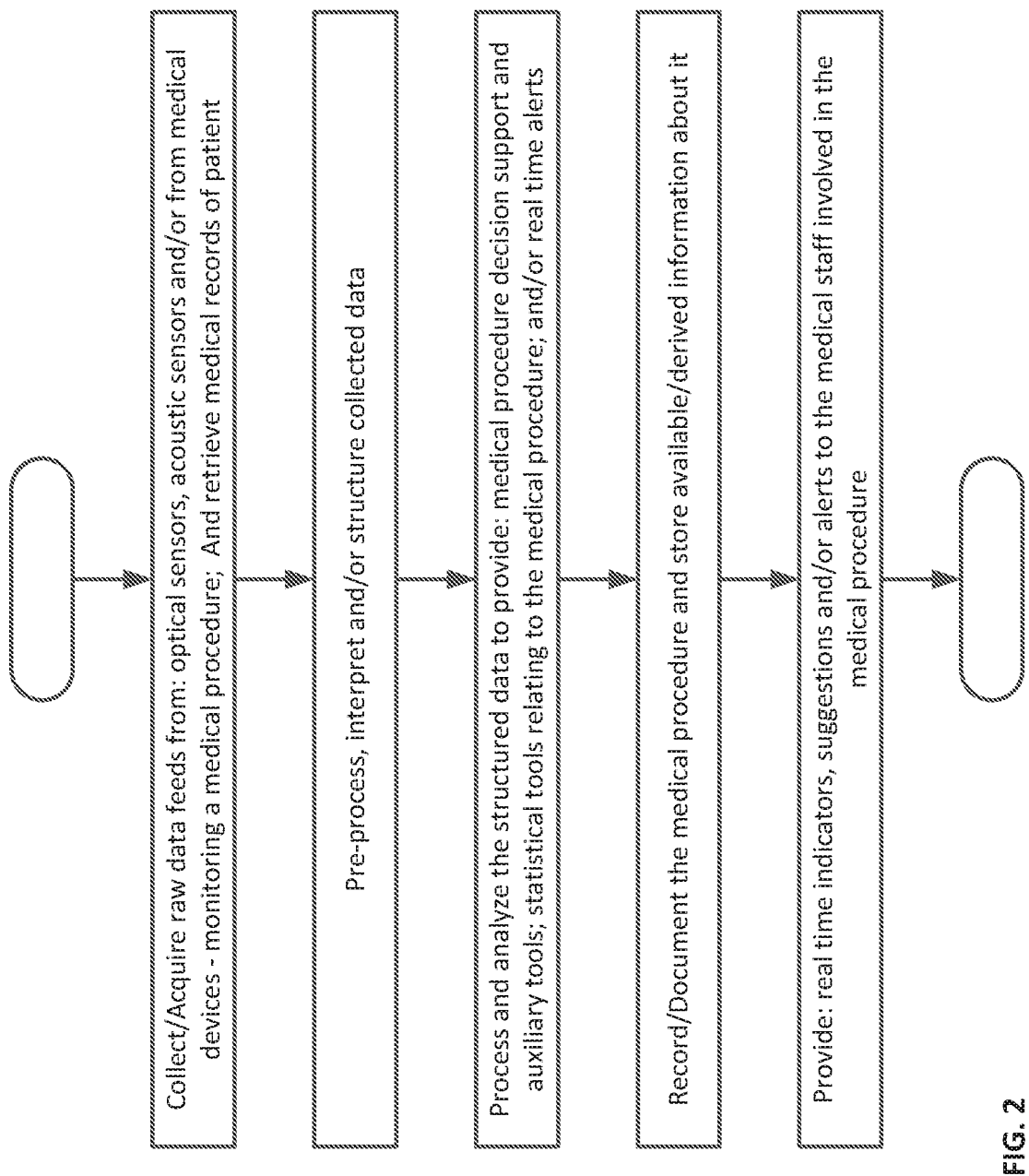
FIG. 2 is a flowchart of the main steps taken as part of a process for tracking, evaluating and facilitating medical procedures, in accordance with some embodiments.

In FIG. 2, there is shown a flowchart of the main steps taken as part of a process for tracking, evaluating and facilitating medical procedures, in accordance with some embodiments. Shown process steps, include: collecting raw data from: optical sensors, acoustic sensors and/or from medical devices—monitoring a medical procedure; pre-processing, interpreting and/or structuring collected data; processing and analyzing the structured data to provide: medical procedure decision support and auxiliary tools, statistical tools relating to the medical procedure and/or real time alerts/notifications; recording the medical procedure and storing available/derived information about it; and providing real time indicators, suggestions and/or alerts to the medical staff involved in the medical procedure.

Figure 3:
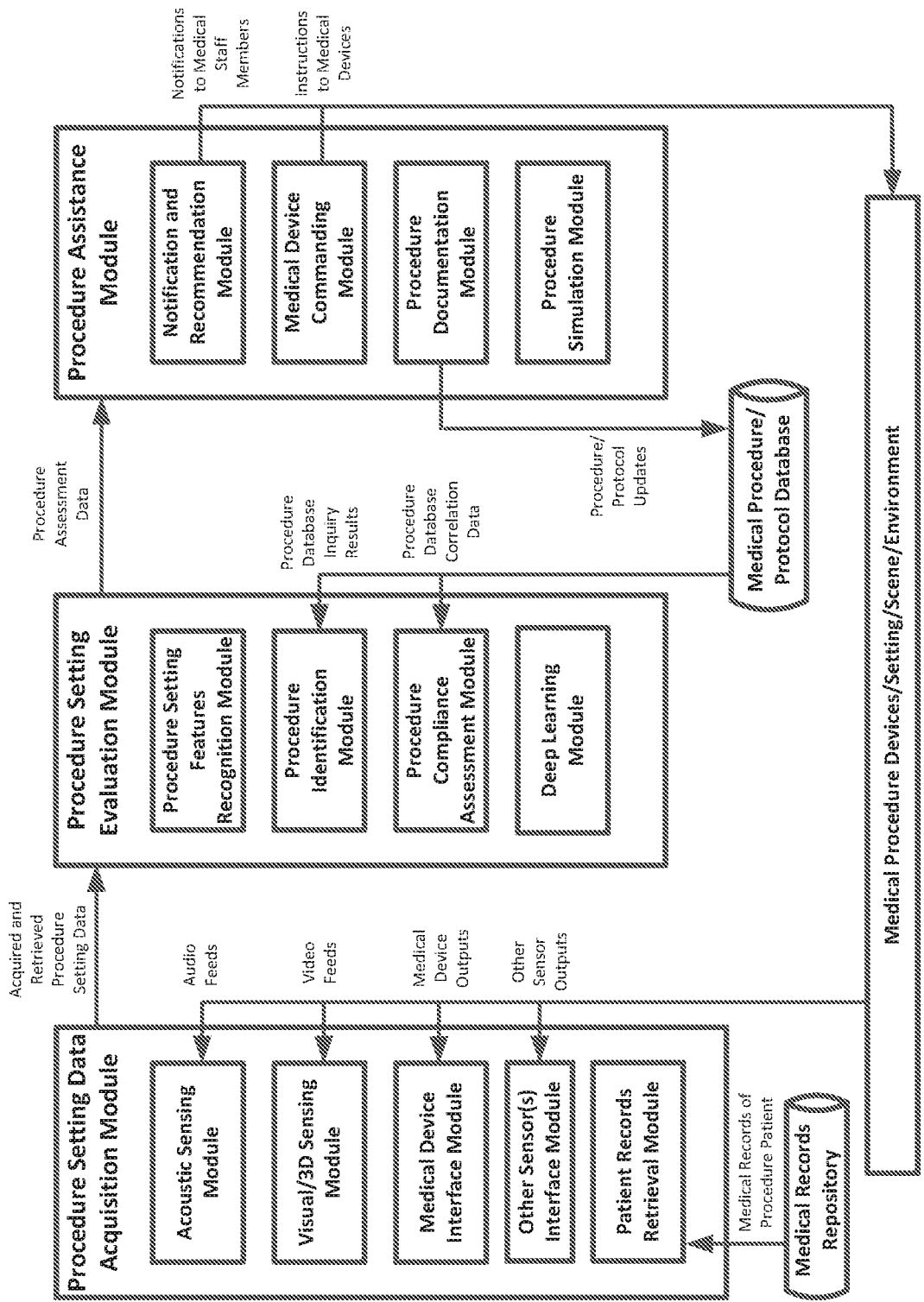
FIG. 3 is a block diagram of an exemplary system for medical procedure tracking, evaluation and facilitation, including system modules and their interrelations, in accordance with some embodiments of the present invention.

In FIG. 3 there is shown, in accordance with some embodiments of the present invention, a block diagram of an exemplary system for medical procedure tracking, evaluation and facilitation, including system modules and their interrelations.

In the figure, three main system modules, or system blocks, are shown—a procedure setting data acquisition module, a procedure setting evaluation module and a procedure assistance module. The procedure setting data acquisition module, includes an acoustic sensing module, a visual sensing module and a medical device interface module, shown to respectively acquire audio feeds, video feeds and medical device output feeds, from a medical procedure setting/scene. The procedure setting data acquisition module is shown to further include a patient records retrieval module, referencing a medical records repository to retrieve medical records of the patient being treated as part of the medical procedure.

The procedure setting evaluation module, receives the acquired and retrieved procedure setting data and a procedure setting features recognition module detects and extracts features from within the data. A procedure identification module utilizes the extracted features and results of inquiries to medical procedure database, to identify the procedure being carried out and optionally specific stages/steps thereof. A procedure compliance assessment module, correlates the extracted features to the identified procedure and assesses the compliance of the features with the identified procedure records. A deep learning module generates further understandings in regard to the procedure, to yield further conclusions relating to the procedure and/or validate ones reached by the procedure compliance assessment module.

The procedure assistance module, receives the procedure assessment data, based on which notifications, instructions, data updates and performance evaluations, are generated. A notification and recommendation module generates and outputs notifications to medical staff members; a medical device commanding module generates and outputs instructions to medical device; a procedure documentation module generates and registers procedure protocol updates; and a procedure simulation module generates evaluations relating to the performance of medical staff members participating in the procedure.

Procedure Setting Data Acquisition Module

Data acquisition and collection, in accordance with some embodiments of the present invention, may include the collection of raw data from the various sensors, medical devices and medical data sources. Each data type may be interpreted separately, or in connection with other data types, and relayed to processing and analysis modules/units of the system to derive understanding of medical procedure setting.

According to some embodiments of the present invention, the data collected by the system may be at least partially collected in substantially real time. Collected data may be interpreted and structured, prior to its analysis. Various image, sound and/or general data, pre-processing and/or processing techniques, may be implemented on the collected data. For example—a voice stream may be interpreted/transcribed into text, while image or video may be interpreted into physical data, such as: colors, borders, objects, faces, etc.

A system in accordance with some embodiments, may include one or more sensors for monitoring the environment/setting of a medical procedure; and/or one or more medical device interfaces for receiving inputs from medical devices monitoring the medical procedure and/or the treated subject thereof. The system may retrieve additional historical data about the patient stored in other systems such as a central medical records repository. The sensors may acquire procedure environment signals/inputs associated with: the treated subject, the medical staff carrying out the procedure, devices and objects in the environment, the location of the procedure within the medical facility and/or any other medical procedure environment related source.

According to some embodiments, system sensors may provide medical parameters, or information about the flow of the procedure. System sensor and interface types, may include any combination of the following.

Figure 4A:
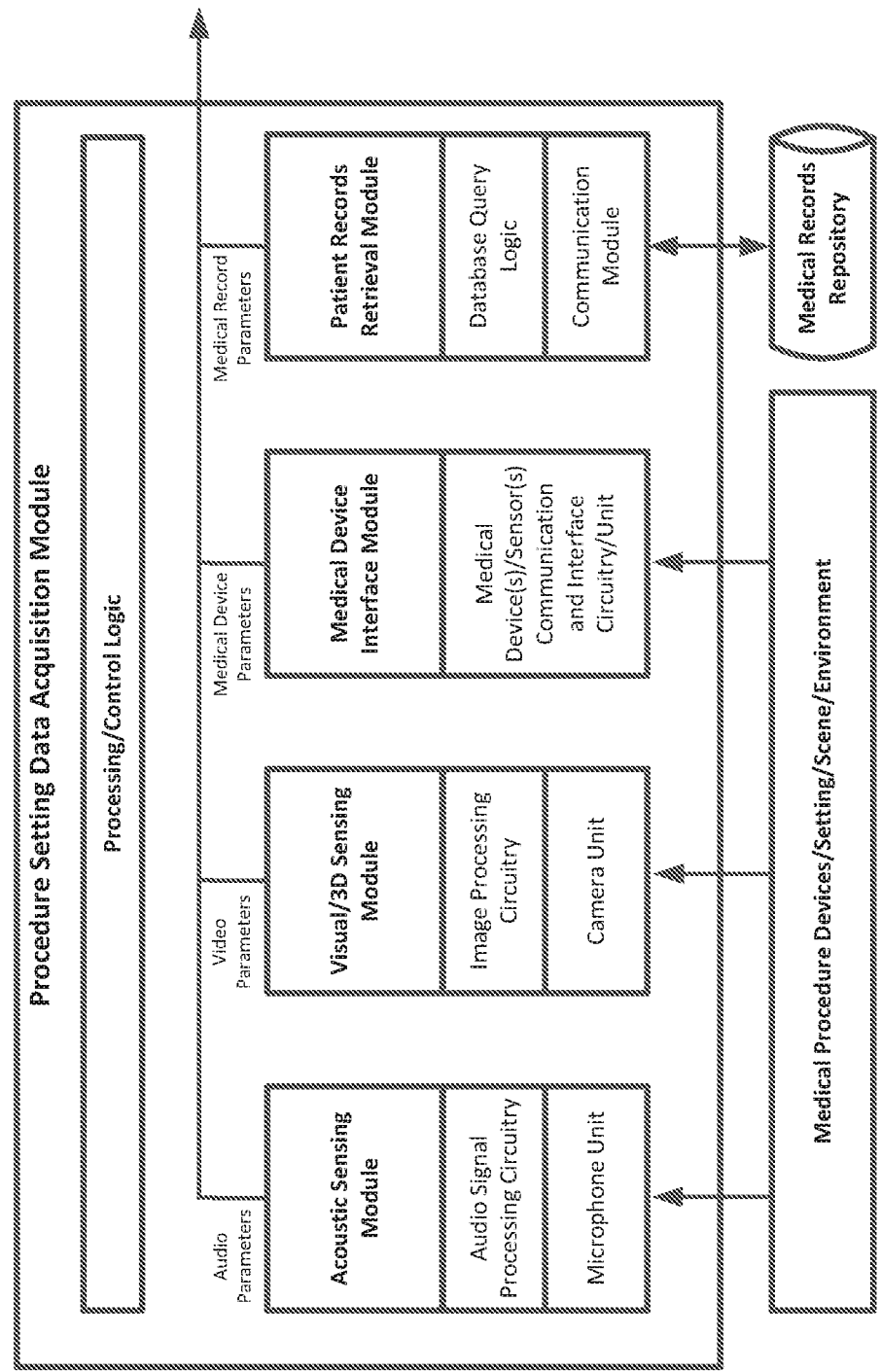
FIG. 4A is a block diagram of an exemplary procedure setting data acquisition block/module, including sub-modules, components and logics and their interrelations, in accordance with some embodiments of the present invention.

In FIG. 4A there is shown, in accordance with some embodiments of the present invention, a block diagram of an exemplary procedure setting data acquisition block/module, including sub-modules, components and logics and their interrelations.

The procedure setting data acquisition block/module includes an acoustic sensing module for acquiring audio feeds from the setting of the medical procedure by utilizing its shown microphone unit. Audio feed signals are then processed by an audio signal processing circuitry to yield a data set of audio parameters.

The procedure setting data acquisition block/module includes a visual sensing module for acquiring video feeds from the setting of the medical procedure by utilizing its shown camera unit. Video/image feed signals are then processed by an image processing circuitry to yield a data set of video parameters.

The procedure setting data acquisition block/module includes a medical device interface module for acquiring output feeds from medical devices monitoring the procedure treated patient by utilizing its shown medical device communication and interface circuitry. Medical device signals are then processed by the circuitry to yield a data set of medical parameters.

The procedure setting data acquisition block/module includes a patient records retrieval module for retrieving procedure treated patient medical records by utilizing the shown communication module to reference a medical records repository with medical records repository/database queries generated by the database query logic. Medical record parameter data representing the retrieved records processed by the module, is then yielded.

Acoustic Sensing Module

Voice/Sound data may be acquired from the medical procedure setting/environment. The data may be collected/recorded and may include: the voice of the medical staff (each or any of the medical and/or paramedical staff members), the voice of the patient, sounds emitted by other medical devices in the vicinity and/or sounds associated with the general atmosphere in/around the medical environment. Voice data may be collected by a dedicated microphone, or by a set of microphones. Microphone(s) and functionally associated circuitry may, for example, collect the voice/sound of each source around, clean the noise(s) and/or distinguish between the different voices/sounds/speakers around. Distinguished voices/sounds/speakers may be corresponded to specific sources—human and/or non-human—in medical procedure environment.

An Acoustic Sensing Module, or microphone unit, may include a microphone or a set of microphones (for example microphone array) that may pick up and record audio signals data from the medical procedure environment and run pre-processing and/or signal processing tasks over the data. For example, picked up audio signals may be separated into several channels coming from several directions or sources (e.g. several speakers, several equipment types) as part of preparing it for further analysis and/or transcription (translation into text). Recorded audio signals may include any type or combination of: speech, voices, sounds, vibration or mechanically generated sounds and/or any other acoustically obtainable representations.

Visual Sensing Module

Video/Image data may be acquired from the medical procedure setting/environment. The data may be acquired by a camera(s), for example, regular, video, HD, wide angle, 3D and/or infra-red cameras, wherein the camera(s) may be positioned in a location and orientation to enable direct line(s) of sight to the medical procedure being carried out. The data may be collected/recorded and used to produce video or images from which valuable procedure related information may be derived.

A Visual Sensing Module, or camera unit, may include an optical acquisition component or set of components that may obtain images of the medical procedure environment and apply image/signal processing techniques/algorithms thereto. Acquired images may include any type or combination of: still images, video, 2-dimensional images, multiple 2-dimensional images, 3-dimensional images, 3-dimensional maps and/or any other optically obtainable representation.

Medical Device Interface Module

Medical procedure setting/environment data may be acquired by integration with medical equipment and devices, wherein the system may interface with and receive information from functionally associated and/or communicated medical device(s) and store it. The information may be received from external sensors (e.g. sensors of other medical devices) and/or from sensors that are part of the system and are adapted to monitor and collect data associated with external/other medical devices associated with the medical procedure and or present in its environment.

A Medical Device Interface Module, or unit(s), may be functionally associated/integrated with, or communicatively networked to, one or more medical devices and/or medical equipment types in the medical procedure environment. The association, integration and/or networking of the system to the medical devices/equipment may utilize a medical device interface unit/device, for example, in the form of: a cable, an adapter, a system port and connector, an antenna/receiver/transmitter for wireless communication, the directing of an inputs device (e.g. camera, microphone) to an output device (e.g. display, speaker) and/or the like. Some or all of the interface units/devices may include hardware elements (e.g. control/logic circuitry), software elements (e.g. execution/operation instructions/schemes, device drivers) and/or both. System associated/integrated medical devices may for example include, but are not limited to: a sphygmomanometer, a thermometer, a Computed Tomography (CT) scanner, an Oxygen saturation monitor, Electrocardiography (ECG) and/or others. Data from the associated/integrated medical devices may include any combination of physiological parameters of a monitored patient and/or parameters associated with treatments (e.g. medicine dosages, radiation amounts) received by the patient as part of the medical procedure.

Patient Records Retrieval Module

According to some embodiments, the system may retrieve additional historical data about the patient, stored in other, communicatively associated, system(s) such as, but not limited to, a central medical records repository. The data may, for example, include information about the weight, or body surface area, of a patient and/or data about his medicine sensitivities/allergies, and may be used the system's processing and analysis modules to calculate drug/medicine dosages or to avoid drugs/medicines mismatching the patient's medical records. Such calculation results and/or system recommended medicine selections, may be provided to the medical staff via an output unit as described herein.

A Patient Records Retrieval Module, or unit, may retrieve medical history data about, or records of, the patient—stored on one or more system integrated and/or communicated sources/databases, such as a central medical records repository. Retrieved patient data, may for example include any combination of: prior diagnostics, medical treatments and procedures performed on patient physiological parameters, measurements and indexes of patient; medical test result values; medical treatment/substance sensitivities/allergies; and/or other parameters. The identity of the patient, for data-source/database reference purposes, may be obtained by any combination of: direct entry made by a medical/administrative staff member; correlating patient voices/images/biometric-parameters/physiological-parameters, for example those collected by the visual and/or acoustic sensing modules, with corresponding prior records; correlating patient physiological parameters, for example those collected by the medical device interface module, with corresponding prior records; and/or others patient associated parameters or characteristics.

Procedure Setting Evaluation Module

According to some embodiments of the present invention, collected data may be processed and analyzed to provide some or all of the information types described herein.

A system in accordance with some embodiments, may include one or more processing/analysis units/logics for receiving the information from the sensors, medical device interfaces and/or retrieved medical records. The information may be: filtered, refined, processed, analyzed, compared, and/or correlated as described herein—to evaluate the medical procedure setting.

Figure 4B:
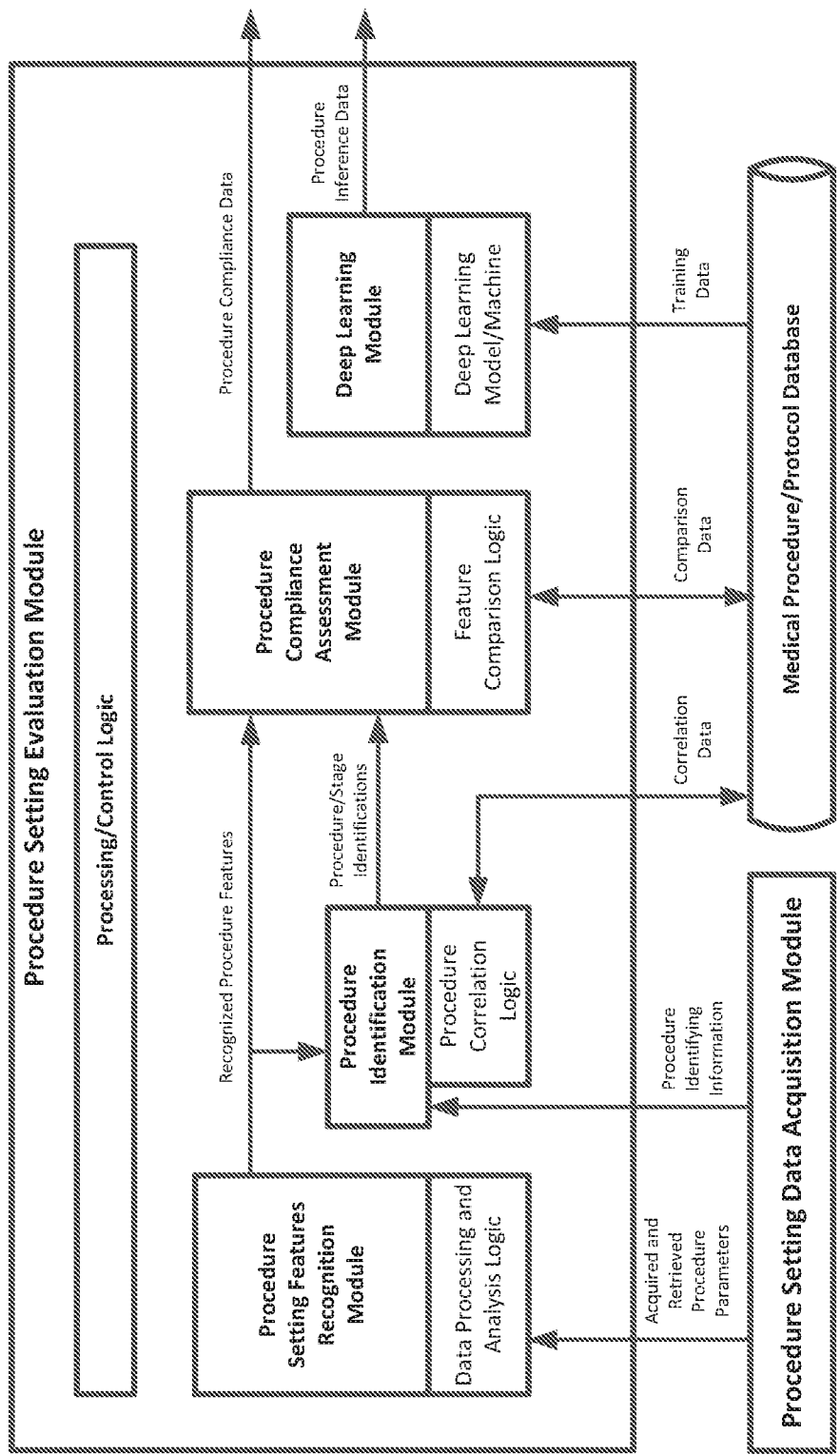
FIG. 4B is a block diagram of an exemplary procedure setting evaluation block/module, including sub-modules, components and logics and their interrelations, in accordance with some embodiments of the present invention.

In FIG. 4B there is shown, in accordance with some embodiments of the present invention, a block diagram of an exemplary procedure setting evaluation block/module including sub-modules, components and logics and their interrelations.

The procedure setting evaluation block/module includes a procedure setting features recognition module having a data processing and analysis logic to detect, recognize and extract procedure features from the acquired and retrieved procedure parameters.

A procedure identification module, utilizes a procedure correlation logic to reference a medical procedure/protocol database with procedure identifying information and the recognized procedure features, identifying the type and stage of the medical procedure being carried out.

A procedure compliance assessment module utilizes a feature comparison logic to reference the medical procedure/protocol database with procedure/stage identification information and the recognized procedure features, generating procedure compliance data of the procedure with the procedure protocol records in the database.

A deep learning module generates further understandings in regard to the procedure, based on procedure protocol training data learned, to yield further conclusions relating to the procedure and/or validate ones reached by the procedure compliance assessment module.

Procedure Setting Features Recognition Module

A Procedure Setting Features Recognition Module, or unit, may detect, extract and/or recognize features from the medical procedure setting, wherein features may include any combination of: medical procedure staff members; the subject/patient being treated as part of the medical procedure; and/or equipment, devices, tools and/or medications/drugs present in the medical environment. Extracted features may be detected, may include, may be characterized and/or their type/role/action/activity may be recognized, based on a combination of: acoustic sounds and/or statements/expressions, in the acquired audio data/recordings, associated therewith, shapes, positions and/or orientations, in the acquired images/video, associated therewith; medical values and/or information, in the acquired medical device/equipment parameters, associated therewith; and/or personal data and records, in the retrieved medical patient records, associated therewith.

According to some embodiments, the procedure setting features recognition module may include audio signature detection functionality for correlating detected sounds—for example, utilizing speaker recognition and/or speech recognition technologies/methodologies implementing logic(s)/circuits—with specific actions, specific medical equipment usage, specific medical tools usage and/or specific chemicals/medicines/drugs usage.

According to some embodiments, the procedure setting features recognition module may include video signature detection functionality for correlating detected images—for example, utilizing optical face/movement recognition and/or optical item identification technologies/methodologies implementing logic(s)/circuits—with specific actions, specific medical equipment usage, specific medical tools usage and/or specific chemicals/medicines/drugs usage.

According to some embodiments, the procedure setting features recognition module may include medical parameters assessment functionality for correlating—for example, utilizing data inputs received from the medical device interface module logic(s)/circuits—with specific medical conditions, treatment reactions, medicine responses, deviation/divergence beyond threshold values of a physiological parameter or set of parameters and/or any type of medical diagnosis.

According to some embodiments, the procedure setting features recognition module may include medical parameters past records based assessment functionality, wherein medical parameters may be assessed and correlated, at least partially in connection with corresponding patient history records parameters, in data inputs received from the patient records retrieval module.

According to some embodiments, results from any combination of the: audio signature detection functionality, video signature detection functionality, medical parameters assessment functionality and/or patient records retrieval module, may be cross correlated, by the procedure setting features recognition module, for decision making and/or decision verification purposes, associated with procedure setting/environment feature detection, recognition, identification and/or assessment.

Procedure Identification Module

By identifying the medical procedure and understanding its current stage, the system may indicate it, provide information about the current or following stage(s) of the procedure; and/or, may provide additional tools, such as but not limited to: timers, calculators for medication (as medicine dosage) and/or various additional tools required as part, or in support, of the medical procedure or step.

A Procedure Identification Module, or unit, may intermittently reference a Data-Source/Database including reference records of multiple medical procedures, for example, procedure related: medical terms, methodologies, techniques, processes, equipment and tools involved, patient's typical physiological parameters, operation/complication scenarios and/or scenarios' reaction schemes.

Extracted/Recognized features and their related audio data, image data and/or medical device data—of the medical procedure being carried out—may be compared, correlated and/or matched to records in the medical procedure/protocol database, thereby identifying their specific corresponding medical procedure and/or specific/current stage(s) thereof.

Procedure Compliance Assessment Module

A Procedure Compliance Assessment Module, or unit, may compare one or more of the medical setting related features detected/recognized by the Procedure Setting Features Recognition Module to a list of characteristics—for example, expected actions or equipment usages within the reference records of multiple medical procedures—associated with the specific procedure, and/or specific procedure step(s), identified by the Procedure Identification Module as being performed/carried-out in the procedure setting.

Mismatchings, deltas, or deviations/divergences, between medical setting/scene features and respective reference records of the identified procedure/steps, and/or differences/divergences there between, may be registered. Mismatchings or deltas may for example include: differences in the positions and/or orientations of medical staff members and medical equipment or devices: procedure step actions not performed or performed differently from their respective description in the procedure records; commands or requests by medical staff members and medical equipment or devices, not executed; medical staff members and medical equipment or devices not present at the procedure setting; auxiliary medical support and decision support tools and resources not present, not being used, or being used not in accordance with the procedure records; medicines/drugs given to the patient at times and/or dosages mismatching the procedure records; measured physiological parameters deviating/diverging from those that are typical for the procedure; and/or other.

Artificial Intelligence/Deep Learning Module

According to some embodiments, medical procedure setting analysis for medical condition diagnosis and treatment recommendation, may, for example, be achieved using a rule-engine and/or rule-sets.

According to some embodiments of the present invention, an Artificial Intelligence Module may include one or more Deep Learning machines/models for medical condition diagnosis and treatment recommendation.

According to some embodiments, sets of data parameter inputs of specific monitored medical procedures or procedure stages, previously received from the procedure setting data acquisition module, documented/logged and associated with one or more matching diagnosis conclusions and/or treatment recommendations—may be provided to a deep learning machine/model of the artificial intelligence module, as training data.

The trained machine/model may later analyze data parameter input set(s) of a newly monitored medical procedure or procedure stage, using accumulated training knowledge of substantially similar (e.g. past data parameter input sets found by the trained model/machine to be highly-correlated/substantially-similar) past procedures/procedure-stages and their respective diagnostics and recommendations—to diagnose the condition of the patient in the newly monitored medical procedure or procedure stage; and/or or to provide treatment recommendations matching to the newly monitored medical procedure or procedure stage.

The artificial intelligence module, in according to some embodiments, may for example take the form of a deep learning neural network model, trained by supervised-learning, wherein the training data for the model may include sets of audio feeds, video feeds and/or medical device feeds, acquired in connection with a specific medical procedure setting and their corresponding/respective, verified, action recommendations/instructions outputs.

Artificial intelligence module conclusions, diagnostics and/or recommendations may form the entire basis for system outputted conclusions, diagnostics and/or recommendations; and/or alternatively, may be used-to/combined by the system to increase or decrease the validity of (e.g. confirm or negate) conclusions, diagnostics and/or recommendations otherwise reached by the system, as described herein.

Audio feeds related training data sets and later analyzed data set(s), may for example include: sound tone, frequency, volume and/or other acoustic signal parameters.

Video feeds related training data sets and later analyzed data set(s), may for example include: image color, brightness, contrast, pixel change rates and/or other video signal parameters.

Medical device output feeds related training data sets and later analyzed data set(s), may for example include: medical device output signal represented values, signal values deviation/divergence levels, signal values change rates and/or other medical device output signal parameters.

According to an exemplary medical procedure deep learning based analysis scenario, in accordance with some embodiments, inputs throughout a medical resuscitation procedure may be analyzed, to get improved diagnostic understanding of the condition of the patient through the resuscitation procedure process and improved treatment/action recommendation at various stages of the procedure process: wherein the improved understanding and recommendation is based on prior inputs collected throughout medical resuscitation procedures and diagnostics/recommendations provided during/to them, determined to be successful.

According to some embodiments, the artificial intelligence module, in accordance with some embodiments, may be utilized for personalized medicine/treatment purposes. Big data sequences of audio feeds, video feeds, medical device feeds—acquired in connection with multiple medical procedure settings of multiple patients—along with general personal information of the patients, medical personal information of the patients and general (non-medical) information related to the medical procedures and their patients—may be provided as training data to a deep learning model/machine.

The big data sequences learned by the deep learning model/machine, may be utilized for generating and providing, for later/newly received patient data sequences, personalized medical diagnostics, solutions and/or recommendations—similar to those provided in the past cases (model/machine learned cases) to-patients/in-procedures which data-sequences are regarded by the deep learning model/machine as similar to the later/newly received patient data sequences.

Medical procedure setting information of the patients may, for example, include, but is not limited to, any acquired medical setting parameter data described herein. Medical personal information of the patients may, for example, include, but is not limited to, any medical parameter data described herein. General personal information of the patients may, for example, include personal patient information such as: age, gender, profession, place of living and/or other. General information related to the medical procedures of patients may, for example, include: time of day of the procedure, date/season of the procedure, weather conditions at the time of the procedure, location of the medical facility where the procedure is being carried-out and/or other.

Procedure Assistance Module

A system in accordance with some embodiments, may include one or more procedure assistance units/logics for providing: notifications, advises, notices, alerts, decision support tools and/or equipment/device operation commands—related to the medical procedure—to the system's output unit(s). Procedure assistance units/logics outputs may also be used for documentation or updating of database records of the medical procedure being carried out or other procedures related thereto—based on the detected and analyzed: audio data, image data associated/integrated medical device data and/or patient medical records; and/or based on their deviation/divergence from existing procedure records.

Figure 4C:
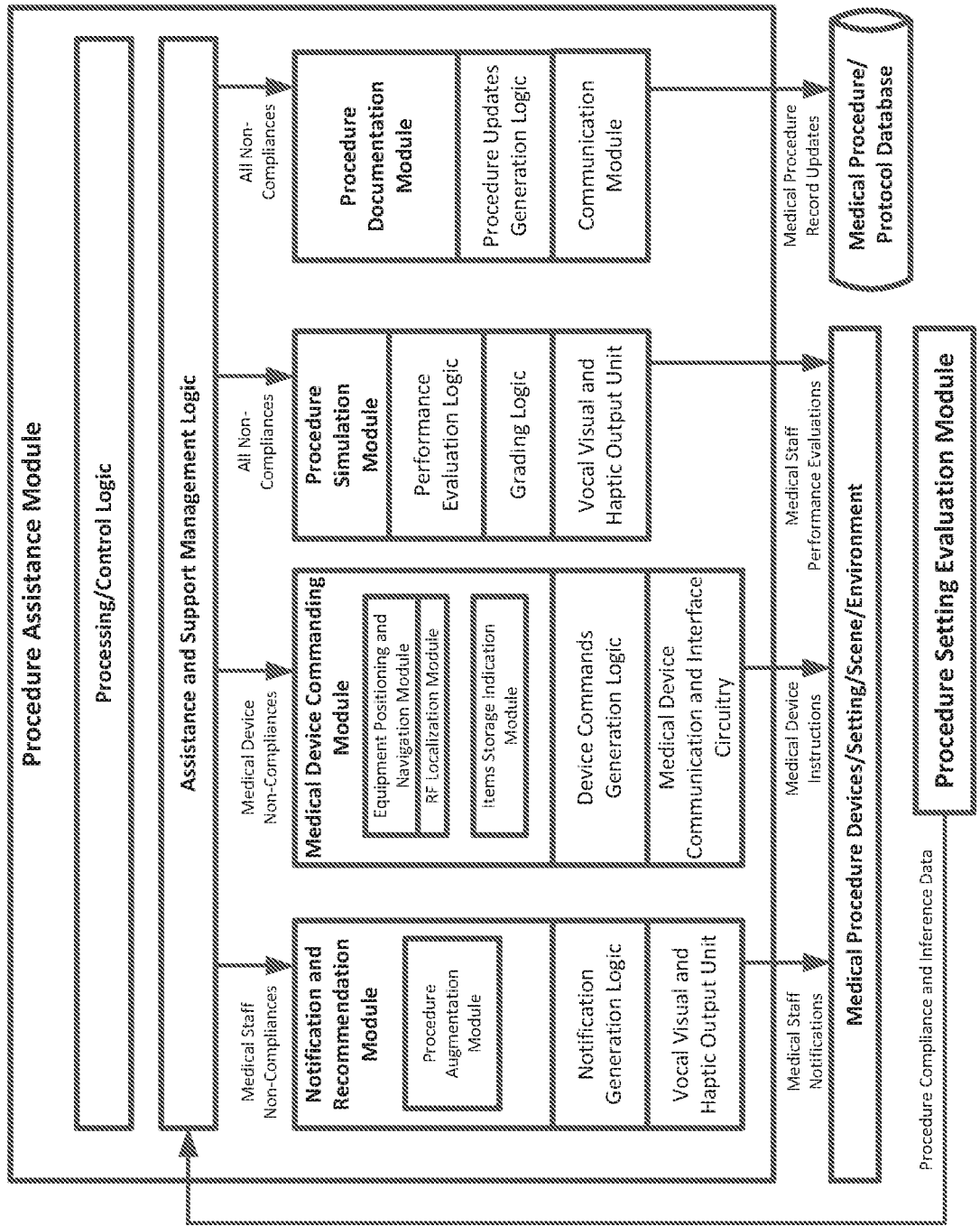
FIG. 4C is a block diagram of an exemplary procedure assistance block/module, including sub-modules, components and logics and their interrelations, in accordance with some embodiments of the present invention.

In FIG. 4C there is shown, in accordance with some embodiments of the present invention, a block diagram of an exemplary procedure assistance block/module, including sub-modules, components and logics and their interrelations.

An assistance and support management logic, distributes medical procedure data analysis results, such as procedure protocol non-compliances, to the sub modules of the procedure assistance block/module.

A notification and recommendation module utilizes a notification generation logic to produce notifications and messages to medical procedure staff members. The notifications and messages are relayed to a vocal, visual and/or haptic output unit for their presentation to the staff members in the procedure setting. A procedure augmentation module, provides medical tools associated with the procedure or its current stage(s), for presentation to medical staff members, thus enhancing, adding-to or improving their performed actions at the procedure setting.

A medical device commanding module utilizes a device command generation logic to produce operation instructions to medical devices in the procedure setting. The instructions are relayed to the medical devices in the setting using a medical device communication and interface circuitry/module. An equipment positioning and navigation module also receives instructions from the device commands generation logic, to locate and navigate medical devices and/or staff members to the procedure setting, wherein location/positioning may be managed by the shown RF localization module. An items storage indication module also receives instructions from the device commands generation logic, to indicate medical devices, tools and items stored within storage unit(s) present at the procedure setting.

A procedure simulation module utilizes a performance evaluation logic to assess the actions of the medical staff members participating in the procedure. A grading logic calculates grades or rankings of the staff members based on their assessed actions, which grades/rankings are relayed to a vocal and visual output unit for their presentation to the staff members in the procedure setting.

A procedure documentation module utilizes a procedure updates generation logic for producing updates to medical procedure protocol database records, based on the evaluation of the current monitored procedure. A communication module relays and registers the produced updates to the database and into the database records.

Notification and Recommendation Module

A Notification and Recommendation Module, or output unit, may issue notifications/advises/notices/alerts to medical staff members, based on the features detected/recognized by the Procedure Setting Features Recognition Module and/or based on their deviation/divergence from, or correlation to, existing procedure records. The Notification and Recommendation Module may trigger the issuance of informative messages to the medical/paramedical staff participating in the medical procedure and/or to other persons (e.g. non-present experts), and/or to machines (e.g. medical computerized platforms or equipment)—associated therewith.

Informative messages, in accordance with some embodiments, may be intended for humans (e.g. take the form of natural-language instructions) and/or, intended for machines (e.g. take the form of: computer commands, parameter values for calculations, database queries) and may, for example, include: notifications of mismatchings with the procedure records; suggestions for actions to be performed in the current, or in a following, procedure step; and/or knowledge augmenting medical calculations, statistics and/or parameters associated with the procedure. The Notification and Recommendation Module or output unit, may distribute/allocate/dispatch/relay the informative data messages to their targeted staff-members/machines, issue respective notifications/indications (e.g. audio, voice, light, visual, haptic) and/or present the information in the messages—visually (e.g. over a display/screen), vocally (e.g. through a speaker), mechanically (e.g. using vibrating units) or in any other way.

Statistical information, in accordance with some embodiments, may be generated based past medical procedures and/or and procedure(s)' decision tree(s) similar to the current procedure. The system may generate/calculate—based on logged/accumulated data from similar procedures and/or known information (e.g. patient characteristics) about the current procedure—statistical information for a specific condition and/or a specific patient, reflecting the statistical meaning/distribution/odds/indexes of each treatment option. For example, in case the medical staff/team should decide between two medications—providing statistical analysis about the effects of each of the two medications, based on past procedures carried-out on substantially similar patients. The effects (e.g. their success rates, their complication rates, their side effects, their level of matching to the characteristics of the current patient) of each of the medications may then be compared to enable a selection of the medication which will yield better results in the current procedure.

System notifications, alerts, messages and/or assistive tools, may be provided substantially in real time and/or may be provided at time points set by the system based on the flow and logic of the medical procedure being carried-out and/or sub steps thereof.

The Notification and Recommendation Module, or output unit, in accordance with some embodiments, may simultaneously retrieve and/or present multiple information sets—including any combination of: the raw data, the analyzed data, the medical records and/or any derivations thereof—to medical staff members taking part in the medical procedure. The data may, for example, be presented in a comparative way, enabling medical staff members (e.g. a physician) to compare, verify and/or select between—multiple options and actions.

Procedure Augmentation Module

According to some embodiments, a Procedure Augmentation Module may provide medical procedure supporting tools and tasks. Procedure supporting tools and tasks may be automatically offered, presented and/or initiated, optionally in connection with, or during, a specific related step of the medical procedure. According to some embodiments, the Procedure Augmentation Module may include and provide an interface for receiving medical staff requests for—medical procedure supporting tools and tasks.

Procedure supporting tools and tasks may, for example, include any combination of: activating timers or stop watches to for timing medical actions, calculating drug dosages, measuring and cross-correlating specific physiological parameters of the patient, retrieving specific information collected or analyzed by the system and/or the like. The medical procedure supporting tools and tasks may augment the work environment of the medical staff members, providing them—over visual, acoustic and/or other output means—with better and more accurate knowledge and control of the medical procedure, as well as better awareness of available procedure options. Some or all of the medical procedure supporting tools and tasks may be provided substantially in real-time.

Medical Device Commanding Module

A Medical Device Commanding Module, or output unit, may issue commands/instructions/requests or provide data to medical equipment or devices, based on the features detected/recognized by the Procedure Setting Features Recognition Module and/or based on their deviation/divergence from, or correlation to, existing procedure records. The Medical Device Commanding Module may trigger the issuance of commands to procedure related machines and devices such as: medical computerized platforms, equipment, mechanical tools, medication providing/giving and physiological support devices, procedure environment conditions related devices (e.g. lighting, temperature) and/or any other system associated therewith.

Medical equipment/device commands, in accordance with some embodiments, may be intended for machines (e.g. take the form of: computer commands, parameter values for calculations, database queries) and may, for example, include: equipment/devices operation initiation or termination; equipment/devices operation manner/intensity changes; addition or removal of scheduled operation/processing/data-registration/data-retrieval tasks, processes or calculations; mobilization and navigation of equipment/devices; storage and location/positioning indication tasks; and others.

Medical Equipment Positioning and Navigation Module

According to some embodiments, there may be provided an autonomous medical device(s), such as medical crash-carts, and medical staff members, location identification and navigation system, the location identification and navigation system may be implemented as a separate/independent/stand-alone system; or, may be implemented as a medical equipment positioning and navigation module, included in a medical treatment procedure tracking, evaluation and facilitation/assistance/support system, in accordance with embodiments of the present invention—wherein medical equipment positioning and navigation capabilities may be triggered as part of the issuance of commands/requests to medical procedure related machines and devices, made by a medical device commanding module in accordance with some embodiments.

According to some embodiments, a first Computerized Smart Remote Device—positioned at a location, or moving through locations, known to a Central Computation Unit—may be initiated/triggered by a user upon an emergency event or medical procedure. The initiation of the first Computerized Smart Remote Device ('Smart Remote' hereinafter) may trigger the generation and relaying of direction and/or navigation instructions to one or more object(s) and/or one or more subject(s) positioned at locations known to, or tracked by, the Central Computation Unit. Generated and relayed instructions may facilitate and/or optimize the ability of the objects and subjects to reach the location of the initiating first Smart Remote (e.g. a medical procedure setting), whether static or dynamic, and to rendezvous thereat.

According to some embodiments, the first Smart Remotes may be: integrated into, connected to, or positioned at the vicinity of, a medical equipment or device (e.g. an emergency room bed) associated with a medical emergency event/procedure of a patient.

The object(s) to which direction and/or navigation instructions are relayed, in accordance with some embodiments, may include one or more medical crash cart(s) each including a respective second Smart Remote utilized for their individual location identification. The medical crash cart(s) and/or second Smart Remote(s) may be communicated/instructed by the Central Computation Unit of the System and provided with the location(s) of the first, emergency event associated, Smart Remote(s) and/or with directions/instructions for navigating to these location(s). Specific directions/instructions for navigation may be provided to each of the one or more medical crash cart(s) depending on their own location(s). The navigation instructions may be translated into one or more mobilization commands relayed to a crash cart mobilization unit or a control logic thereof for execution.

According to some embodiments, the medical crash cart(s) may be fully or quasi-autonomous—enabling a given medical crash cart to substantially independently navigate itself to the location of an initiating first Smart Remote—upon receipt of the position/location of the initiating first Smart Remote, within an environment/facility, from the Central Computation Unit.

The subject(s) to which direction and/or navigation instructions are relayed, in accordance with some embodiments, may be one or more medical staff/team members each carrying a respective third Smart Remote utilized for their individual location identification. The third Smart Remote(s) carried by the medical staff/team members may be communicated/instructed by the Central Computation Unit of the System and provided with the location(s) of the first, emergency event associated, Smart Remote(s) and/or with directions/instructions for navigating to these location(s). Specific directions/instructions for navigation may be provided to each of the one or more medical team members depending on their own location(s). The navigation instructions may be presented through one or more output components (e.g. display, speaker) functionally associated with each of the third Smart Remote(s) of the medical staff/team member users.

According to some embodiments of the present invention, the system may perform one or more of the following tasks: (1) identify the location of the medical event/procedure (or patient), (2) identify the location of—and optionally select/choose—the relevant emergency team member(s) and direct them to the medical event's location, and/or (3) summon/bring the crash cart, or several crash carts, to the location of the medical event, by providing them with the event's location and enabling them to autonomously navigate themselves thereto.

According to some embodiments, medical staff members may be identified by a specific identifier of the Smart Remote that they carry. Specifically identified and localized medical staff members may be selected/chosen for directing to a specific emergency event based on a combination of their location at the time of the event and whether or not they have the skills/expertise needed in order to assist in such an event type (e.g. trauma, cardio, psychiatric, neural).

According to some embodiments of the present invention, the system may identify the location of the medical event/procedure, the location of the crash cart, and the location of any medical team member. By knowing these locations, the system may give (autonomous) navigation commands to the crash cart(s), and relay an event location indicator(s) to the medical team members.

A system in accordance with some embodiments, may include one or more dynamic location identification components, referred to herein as 'Smart Remotes'. The first, second and/or third Smart Remote types described herein may all include substantially similar location identification components; and optionally, one or more additional type-specific components. For example: a given first Smart Remote—associated with the medical-event/procedure/patient—may comprise an emergency event triggering interface and communication components for notifying the Central Computation Unit of the medical event and its location; a given second Smart Remote—associated with the medical crash cart—may comprise an interface to an autonomous mobilization system for automatically moving/driving the cart towards and to the location of the medical event; a given third Smart Remote—associated with the medical team member—may comprise an output component(s) for presenting its medical team member user the location of the medical event/procedure (e.g. as an overlaid position-pin on a map of the facility/environment) and optionally additional event/procedure related data (e.g. initial medical event/procedure related patient-symptoms and/or physiological parameters).

According to some embodiments, the Smart Remotes may take the form of dedicated components—including any combination of circuitry and computer executable code; and/or may be implemented as a physical or logical part—including any combination of circuitry and computer executable code—of an external component or device (e.g. a mobile phone component/application).

According to some embodiments, the system's central computation unit/module may also be interchangeably referred to herein as a 'Local-Hub'). A crash cart containing a control/mobilization unit (hereinafter: 'Control Unit') may send and/or get its location to/from the Local-Hub; and, optionally get navigation commands from the Local-Hub. The Local-Hub may be part of the crash cart's Control Unit or located at another location.

According to some embodiments, the system may further contain or use optional sensors or beacons, to monitor the environment and the location of each Smart Remote associated component—crash cart(s), medical staff member(s) and medical event/patient—in the environment, regularly/intermittently. Location related data may be relayed/sent/communicated to the Local-Hub.

According to some embodiments, using the Smart Remotes, the system may identify the location of the crash cart and/or of the patient in need or procedure setting. The Smart Remotes may be used by medical staff members that carry them while they move; and/or may be deployed/distributed, for example, in: patients' rooms, treatment rooms, another place(s) in the hospital or institute, and/or at any combination of these optional locations. The Smart Remotes may include an option (e.g. a button, an interface) to call the crash cart and/or the medical team (e.g. rapid response team) and/or an option to signal to the system and inform it of their respective locations. When an action is performed using the Smart Remote, such as calling a crash cart, the location of the smart remote may be automatically identified by the system.

According to some embodiments, using the smart remotes that are carried by the medical/emergency team members, and which are on call, the location of the smart remotes and of the team members that carry them may be identified. Using this data, the system may specifically direct each medical team member to the event, find the medical team member(s) closest to the event and/or track the medical staff members.

According to some embodiments, by knowing the location of the crash cart(s) and the location of the medical event destination (i.e. the location of the smart remote that had been activated), the system may navigate the controlled crash cart to the destination, correct navigation errors, and avoid obstacles along the route, during the navigation.

Figure 5A:
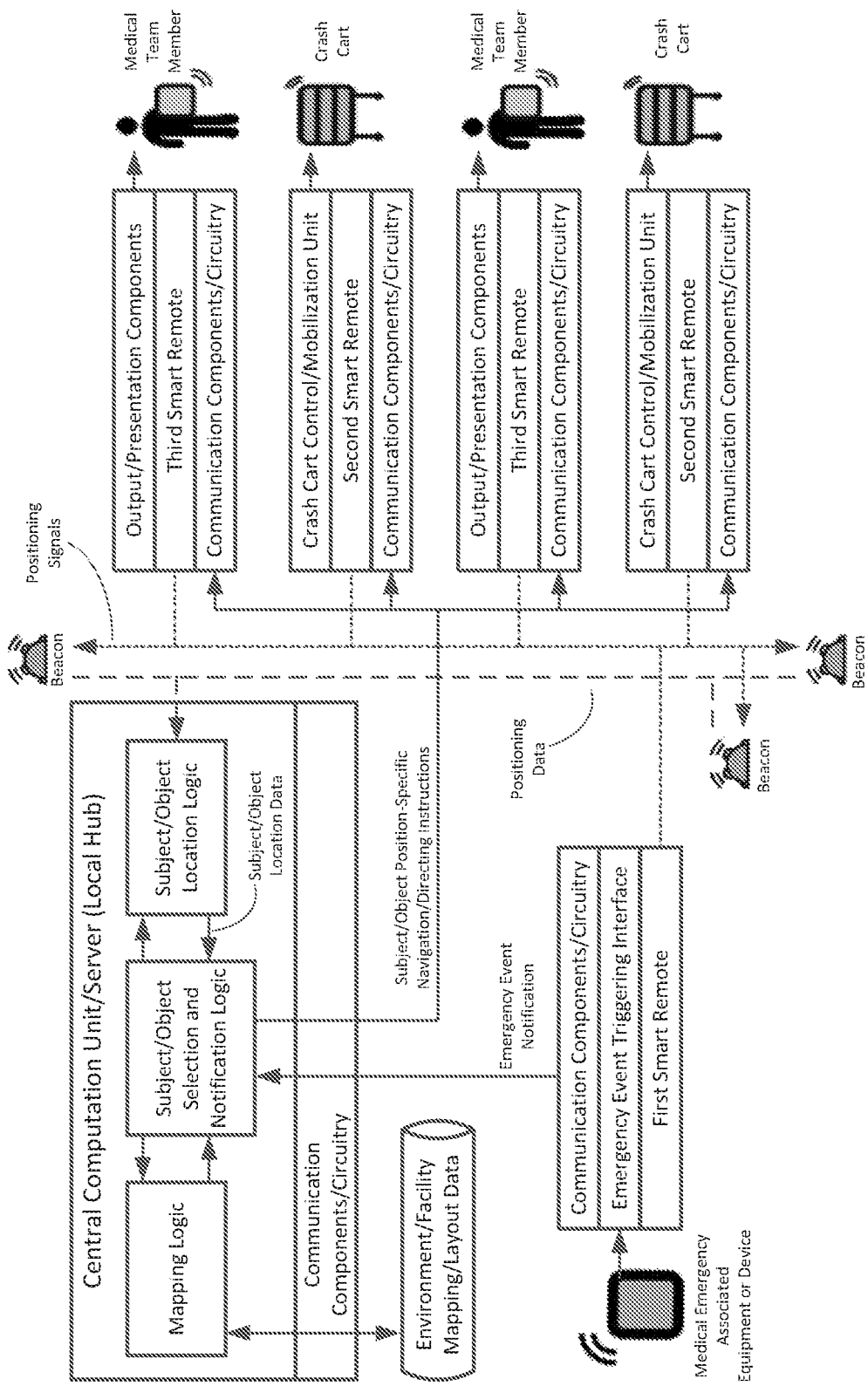
FIG. 5A is a schematic drawing of an exemplary system/module for autonomous crash cart and medical staff location identification, in accordance with some embodiments of the present invention.

In FIG. 5A, there is shown a schematic drawing of an exemplary system/module for autonomous crash cart and medical staff location identification, in accordance with some embodiments; the system is deployed in an environment, for example, a hospital and includes one or more Smart Remote components; the locations of the Smart Remote components are identified within the environment and the components directed towards the location of another—medical emergency related—Smart Remote component.

In the figure there are shown a first, a second and a third smart remote types, respectively connected to or associated with: a medical emergency associated equipment or device, medical crash carts and medical team members. Shown beacons are utilized for identifying and monitoring the locations of the smart remote associated objects/subjects.

Upon user initiation of the shown emergency event triggering interface a notification is sent to the central computation unit of the system. The shown subject/object selection and notification logic, of the central computation unit, uses subject/object location data—from the shown location logic receiving beacon positioning data: and mapping/layout data—from the shown mapping logic referencing an environment/facility mapping/layout database; to identify the location of each of the objects/subjects within the facility (e.g. hospital).

The subject/object selection and notification logic generates and relays specific navigation/direction instructions for each of the subjects/objects—based on their own location in relation to the location of the first smart remote that is associated with the emergency event. Relayed instructions are used by for guiding medical staff member(s) towards the medical emergency event and/or for directing one or more crash cart(s)—for example by generating specific sets of mobilization/traveling commands and providing it to a corresponding set of autonomous crash carts for their execution and arrival at the medical emergency event destination.

According to some embodiments, the central computation unit, or local hub, of the system may, for example, be implemented: as a separate component (e.g. on a remote networked computer/server); as part of, or connected to, the medical emergency associated equipment or device; as part of one or more of the crash carts; and/or as a distributed system having components located at, or along with, multiple other system components.

Figure 5B:
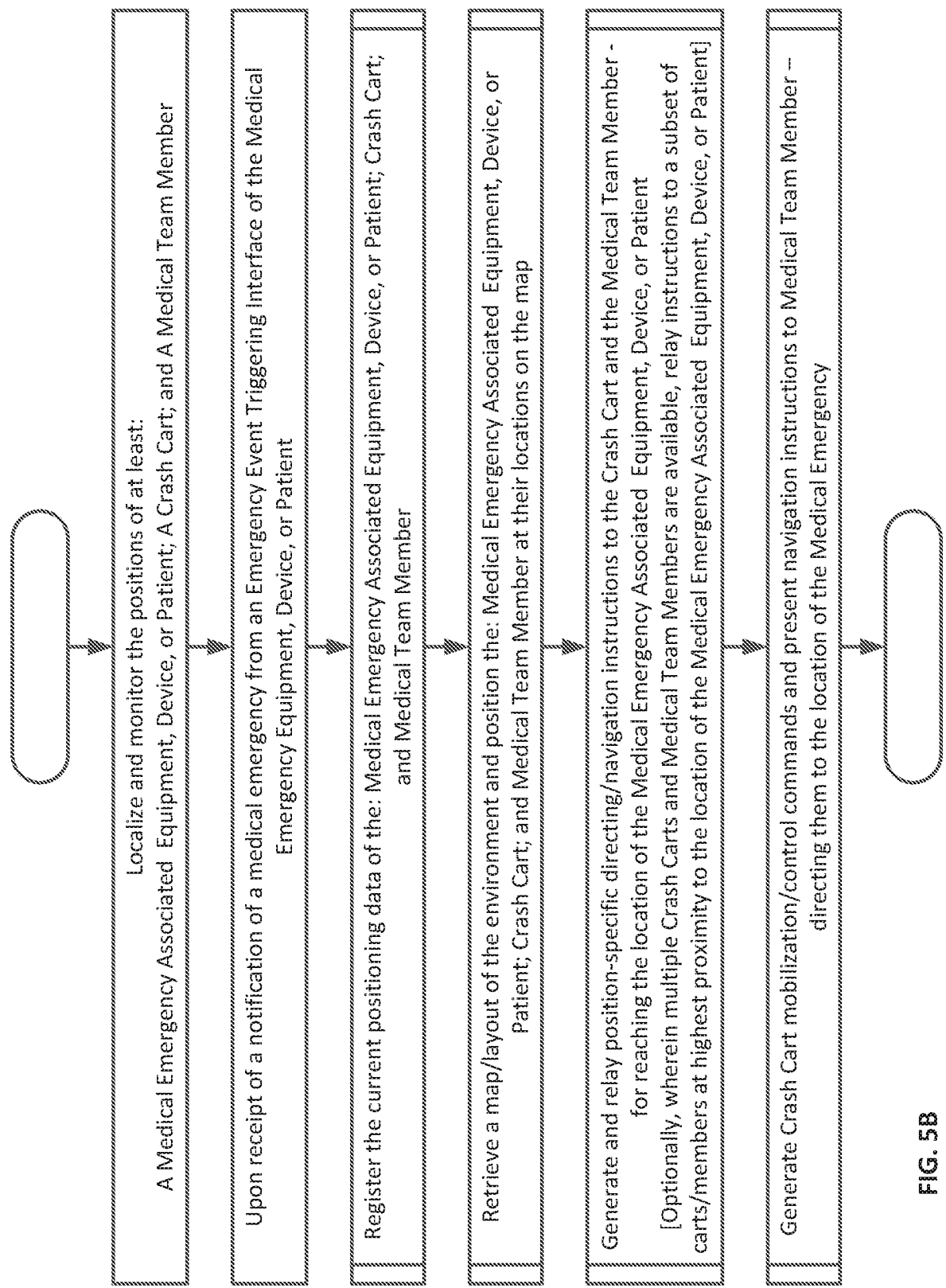
FIG. 5B is a flowchart of the main steps executed as part of an exemplary process for autonomous crash cart and medical staff location identification, in accordance with some embodiments of the present invention.

In FIG. 5B, there is shown a flowchart of the main steps executed as part of an exemplary process for autonomous crash cart and medical staff location identification, in accordance with some embodiments.

Shown exemplary steps, include: (1) Localize and monitor the positions of at least: A Medical Emergency Associated Equipment, Device, or Patient; A Crash Cart, and A Medical Team Member; (2) Upon receipt of a notification of a medical emergency from an Emergency Event Triggering Interface of the Medical Emergency Equipment, Device, or Patient: (a) Register the current positioning data of the: Medical Emergency Associated Equipment, Device, or Patient; Crash Cart; and Medical Team Member; (b) Retrieve a map/layout of the environment and position the: Medical Emergency Associated Equipment, Device, or Patient; Crash Cart; and Medical Team Member at their locations on the map (c) Generate and relay position-specific directing/navigation instructions to the Crash Cart and the Medical Team Member—for reaching the location of the Medical Emergency Associated Equipment, Device, or Patient [Optionally, wherein multiple Crash Carts and Medical Team Members are available, relay instructions to a subset of carts/members at highest proximity to the location of the Medical Emergency Associated Equipment, Device, or Patient]; and/or (d) Generate Crash Cart mobilization/control commands and present navigation instructions to Medical Team Member—directing them to the location of the Medical Emergency.

Figure 6A:
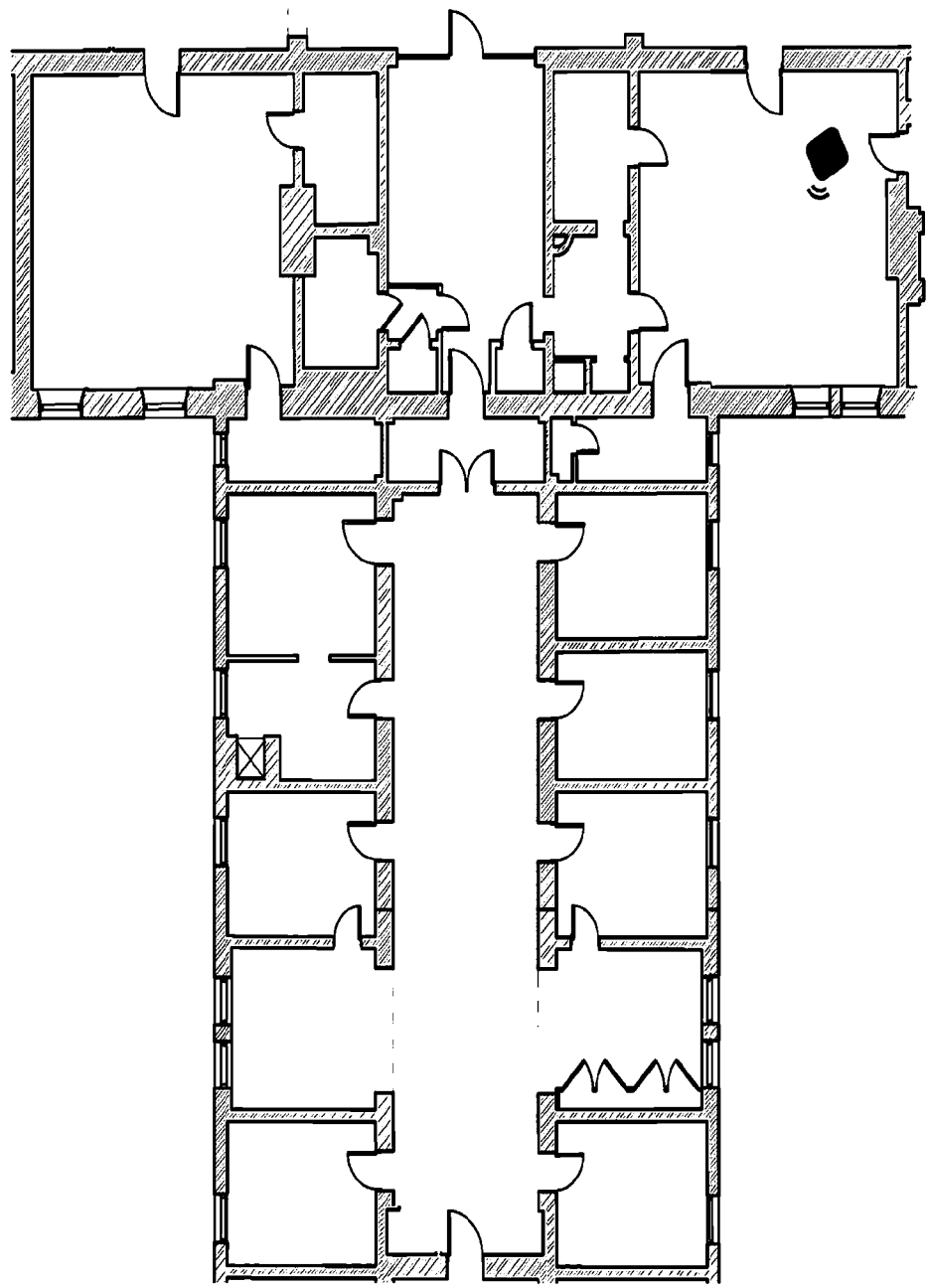
FIG. 6A is a schematic drawing of an exemplary system/module for autonomous crash cart and medical staff location identification, in accordance with some embodiments of the present invention.

In FIG. 6A, there is shown a schematic drawing of an exemplary system/module for autonomous crash cart and medical staff location identification, in accordance with some embodiments; the shown system is deployed in an environment, for example, a hospital, and includes one or more Smart Remote components, wherein one of the Smart Remotes is shown in the bottom right corner of the drawing.

Figure 6B:
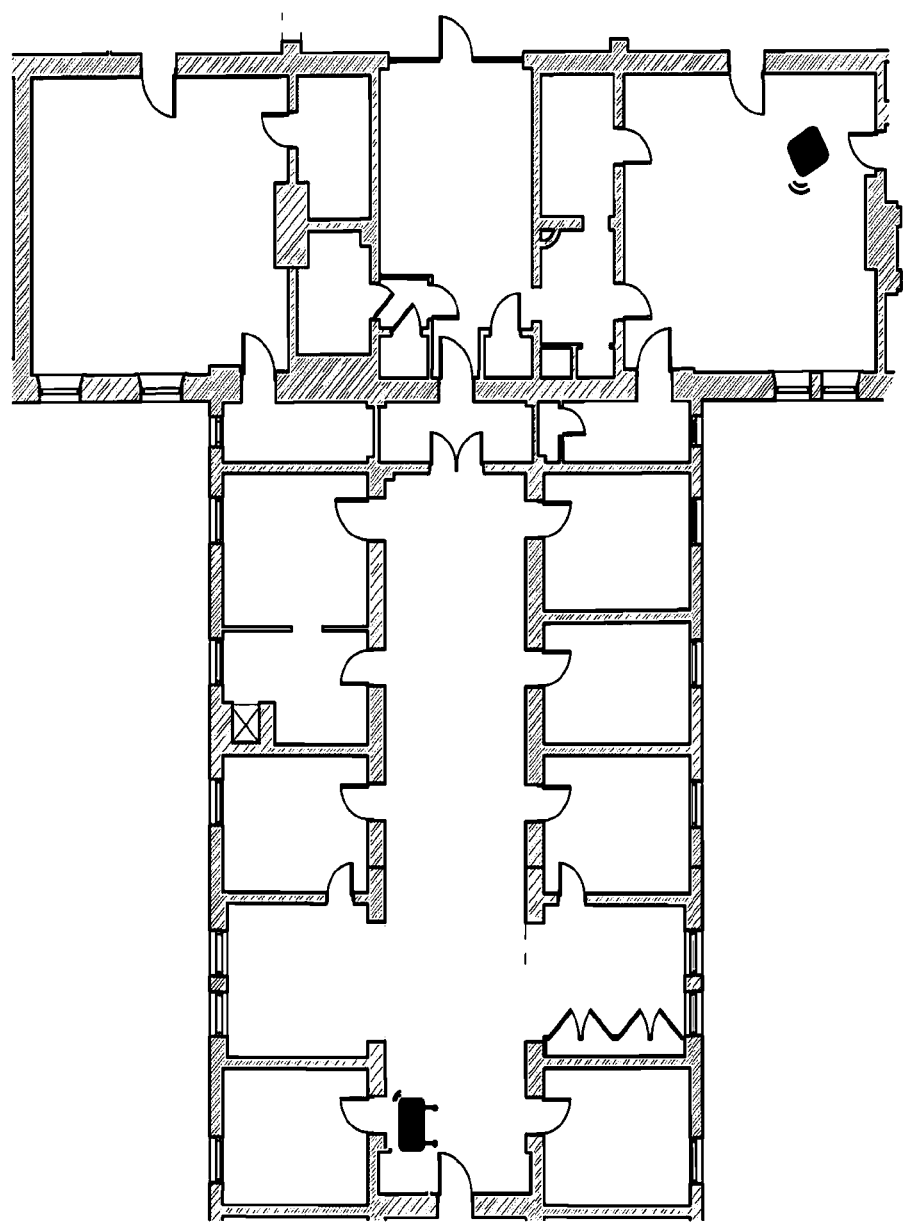
FIG. 6B is a schematic drawing of an exemplary system/module for autonomous crash cart and medical staff location identification, in accordance with some embodiments of the present invention.

In FIG. 6B, there is shown a schematic drawing of an exemplary system/module for autonomous crash cart and medical staff location identification, in accordance with some embodiments; the shown system includes a crash cart including a Control Unit device, wherein the crash cart is shown in the left side of the drawing.

Figure 6C:
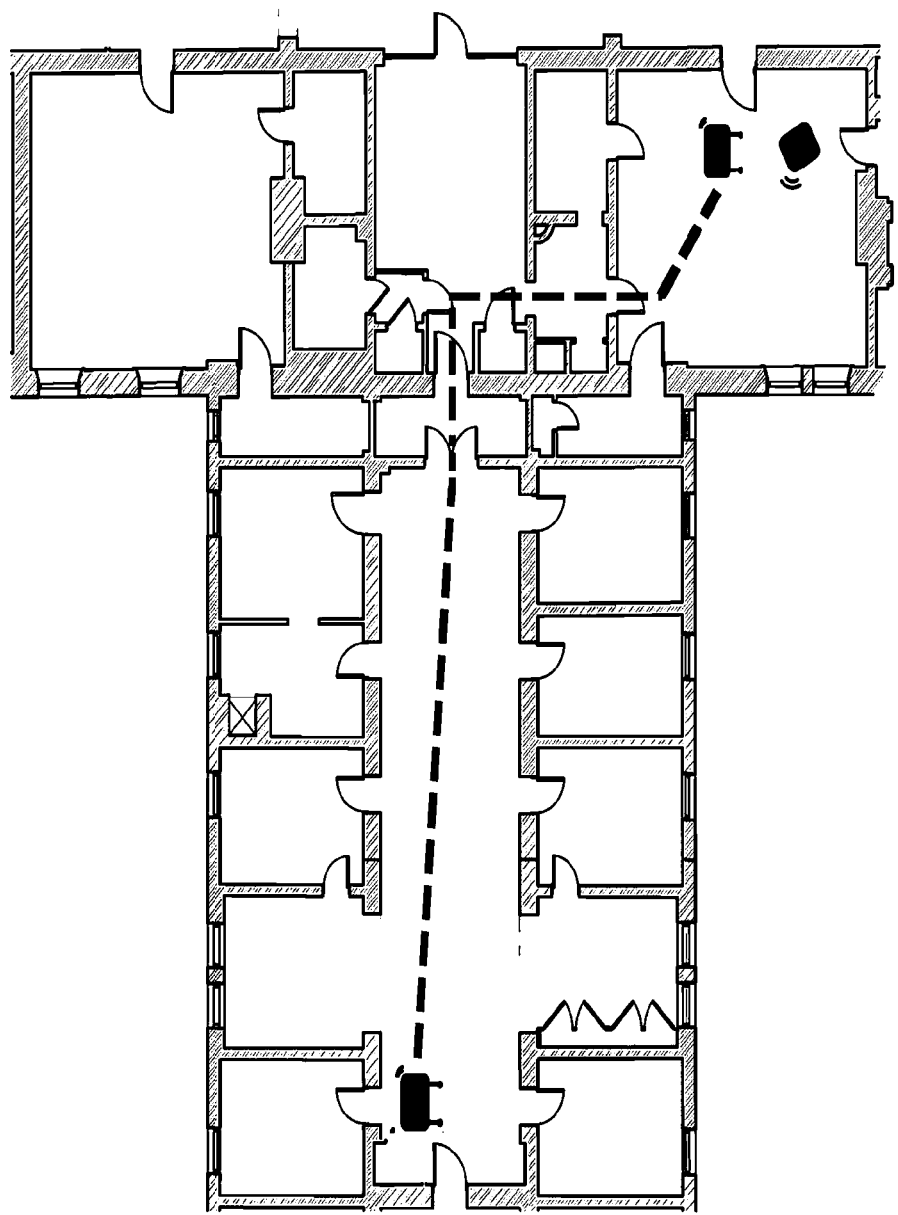
FIG. 6C is a schematic drawing of an exemplary system/module for autonomous crash cart and medical staff location identification, in accordance with some embodiments of the present invention.

In FIG. 6C, there is shown a schematic drawing of an exemplary system/module for autonomous crash cart and medical staff location identification, in accordance with some embodiments; the system is shown after using the Smart Remote to activate a call, wherein the controlled crash cart shown would navigate autonomously—along the broken line—to the location of the Smart Remote.

Figure 6D:
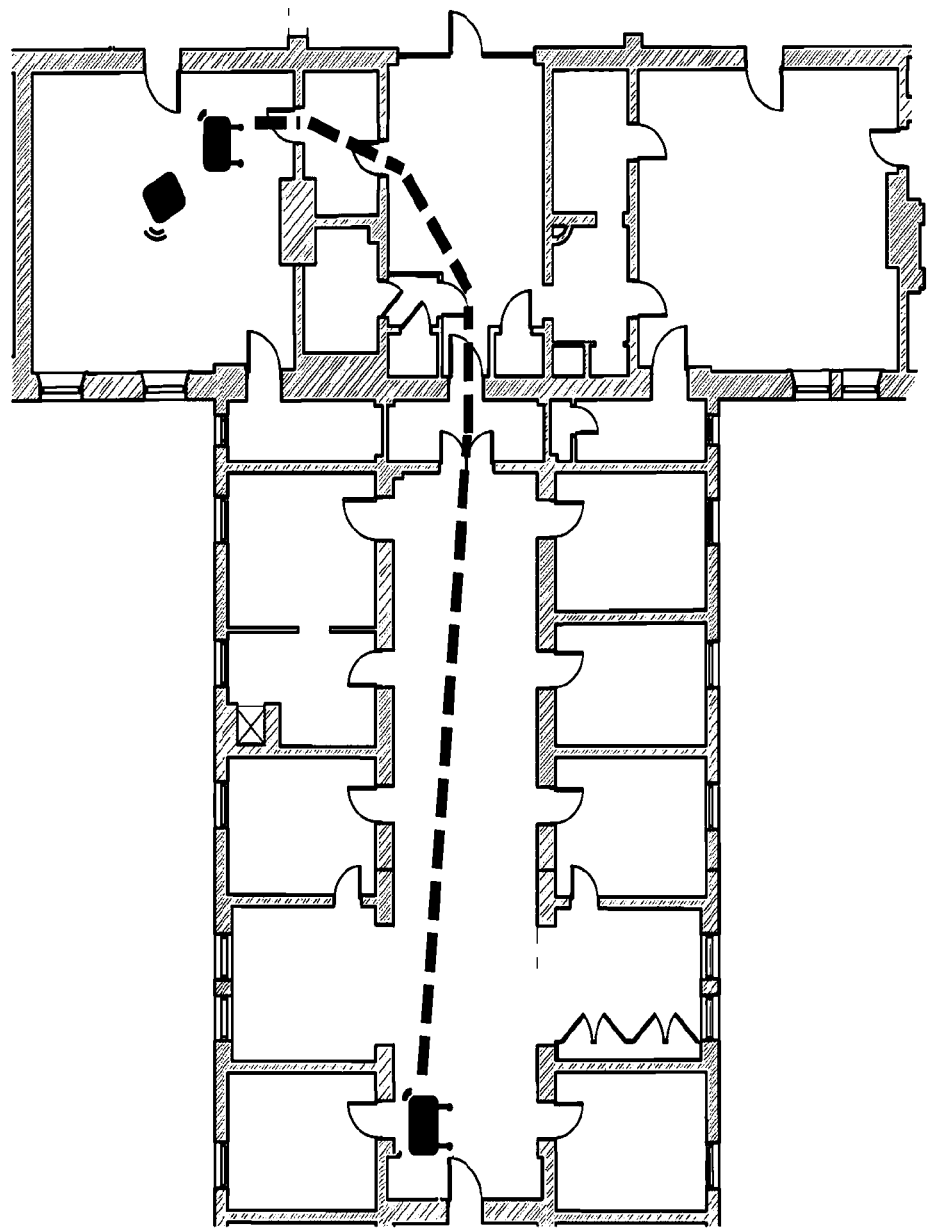
FIG. 6D is a schematic drawing of an exemplary system/module for autonomous crash cart and medical staff location identification, in accordance with some embodiments of the present invention.

In FIG. 6D, there is shown a schematic drawing of an exemplary system/module for autonomous crash cart and medical staff location identification, in accordance with some embodiments; wherein the location of the Smart Remote is changed after it has been used to activate a call, the controlled crash cart follows it and navigates autonomously to the new location of the Smart Remote.

Figure 6E:
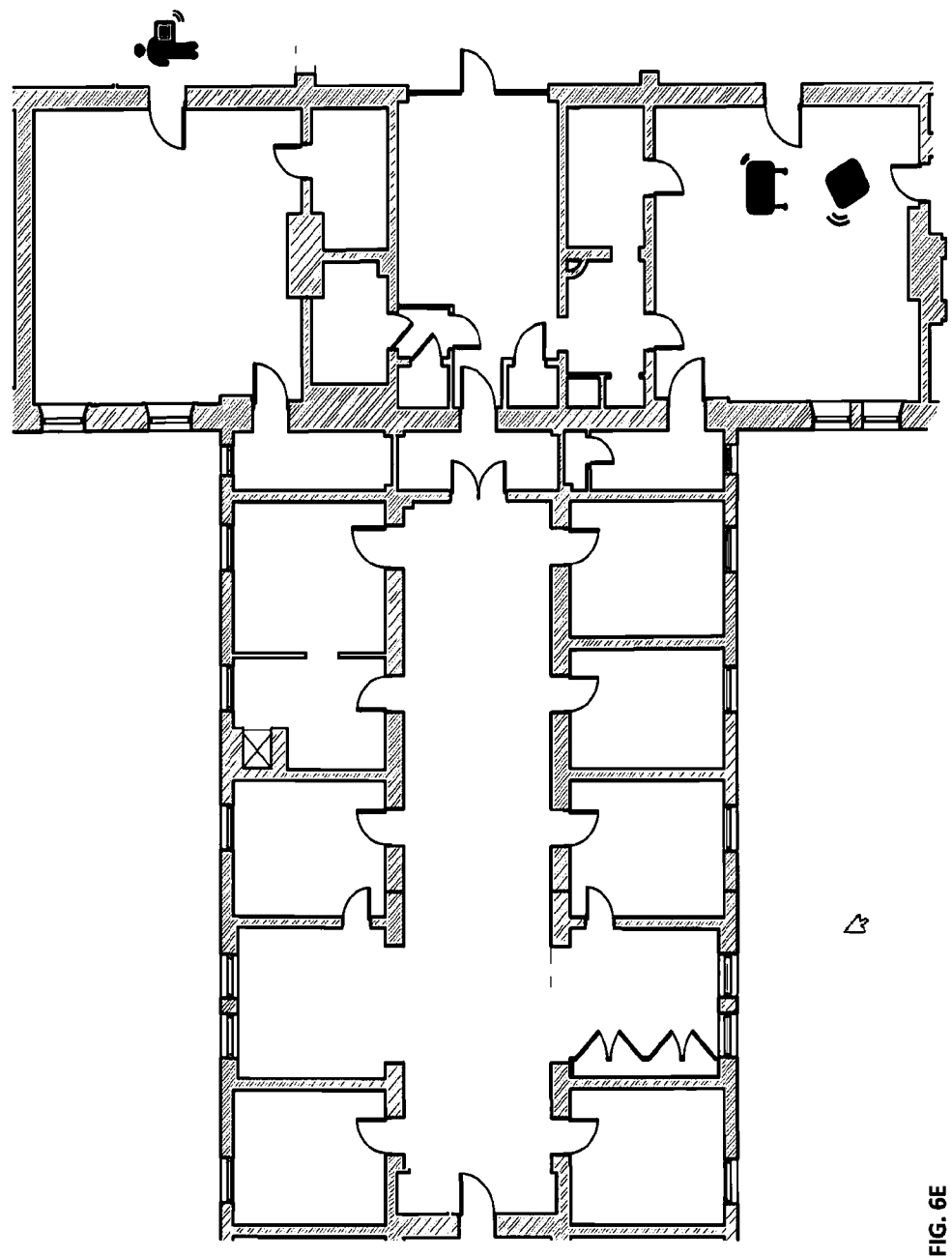
FIG. 6E is a schematic drawing of an exemplary system/module for autonomous crash cart and medical staff location identification, in accordance with some embodiments of the present invention.

In FIG. 6E, there is shown a schematic drawing of an exemplary system/module for autonomous crash cart and medical staff location identification, in accordance with some embodiments: a medical team member holding a smart remote device, or an external device with a smart remote functionality/software, gets the call, with the exact location of the event.

Figure 6F:
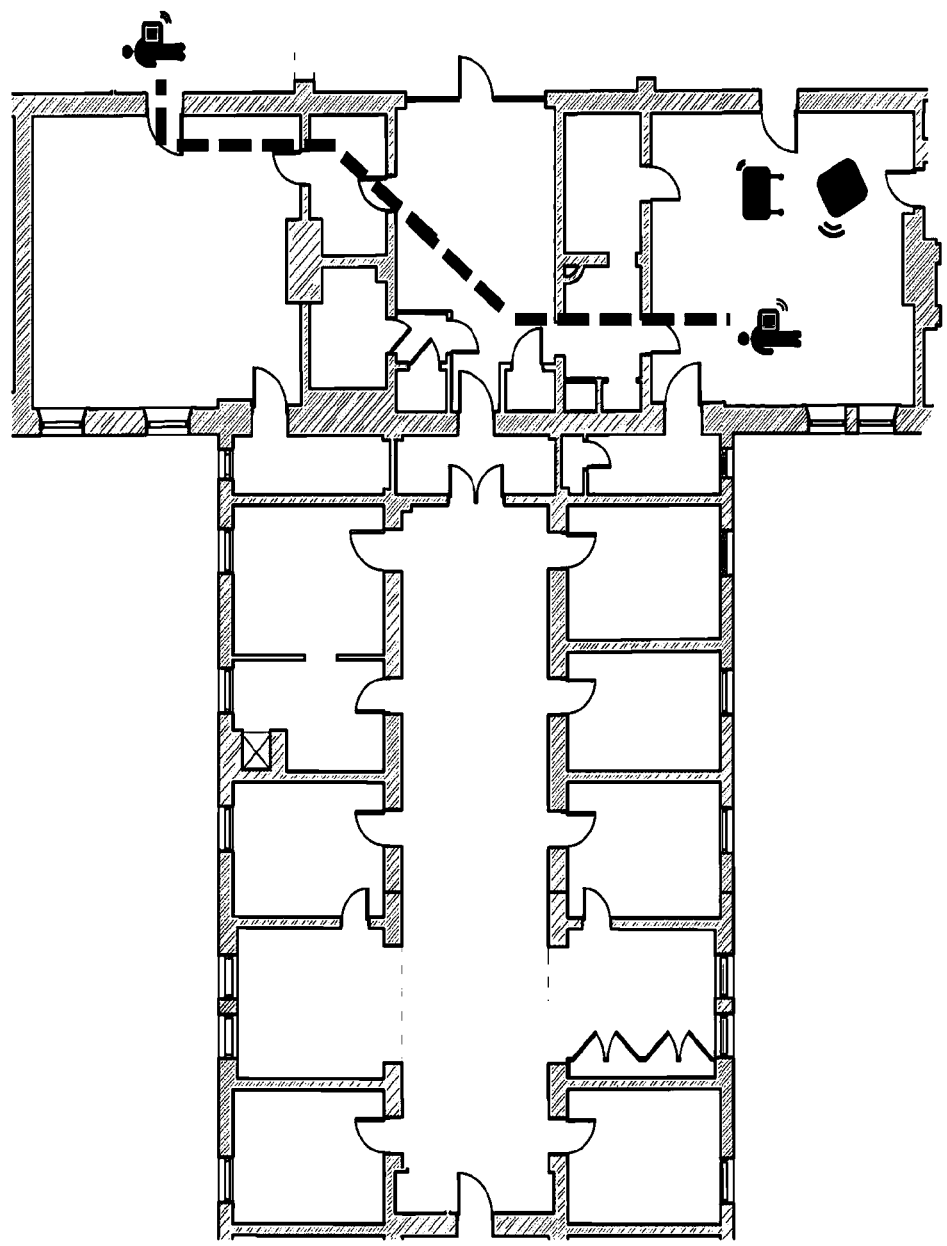
FIG. 6F is a schematic drawing of an exemplary system/module for autonomous crash cart and medical staff location identification, in accordance with some embodiments of the present invention.

In FIG. 6F, there is shown a schematic drawing of an exemplary system/module for autonomous crash cart and medical staff location identification, in accordance with some embodiments; the shown system directs the medical team member to the location of the event; in case the location of the Smart Remote is changed after it has activated a call, the system will follow it and send the medical team member to the new, updated, location of the Smart Remote.

Multi Frequency Based Positioning and Navigation

According to some embodiments, there may be provided a radio frequency (RF) based object localization system, wherein beacon-emitted radio signals tuned to two or more known, different, frequencies, signal-strengths and/or other parameters, are collectively utilized for enhanced localization (e.g. triangulation, fingerprinting or others) of the object(s) within a space or an environment.

The radio frequency (RF) based object localization system may be implemented as a separate/independent/standalone system: or, may be implemented as a radio frequency (RF) based object localization module, included in a medical treatment procedure tracking, evaluation and facilitation/assistance/support system, in accordance with embodiments of the present invention—wherein radio frequency (RF) based object localization capabilities may be utilized as part of medical device(s) (e.g. crash-carts) and staff member positioning and navigation, performed by a medical equipment positioning and navigation module in accordance with some embodiments.

According to some embodiments, beacon-emitted radio signals tuned to two or more known, different, frequencies, signal-strengths and/or other parameters, are collectively utilized for enhanced localization (e.g. triangulation, fingerprinting or others) of the object(s) within a space or an environment.

According to some embodiments, a radio frequency (RF) based object localization module may include one or more transmitter, transceiver and/or beacon type components (hereinafter: 'beacons'. 'beacon components'), the position of which is known, located at different points within the space or the environment; and one or more dynamic receiver, or transceiver, type components traveling/moving/repositioning within the space or the environment. Each of the beacon component(s) may be capable of transmitting/emitting radio signals of at least two different frequencies or frequency ranges; and each of the dynamic components may be capable of receiving radio signals of the at least two different frequencies or frequency ranges.

According to some embodiments, the one or more transmitter, transceiver and/or beacon type components, may include any combination of static and/or dynamic beacon components. The beacon components may be functionally and/or communicatively associated with, or may comprise, a control/management unit.

According to some embodiments, the frequency of the signals transmitted by the beacon components may be intermittently changed/altered, wherein different frequencies are used within different time frames or segments. The frequency of the signals transmitted by each of the beacon components may be substantially simultaneously changed.

According to some embodiments, wherein each of the beacon components also includes a receiver, the changing of the frequency may be synchronized between the multiple beacon components by: a main control unit communicatively associated with each of the beacon components; per-component controllers, of each of the beacon components, wherein the beacon components are communicatively associated with each other and adapted to exchange timestamps or periods for mutual frequency/ies hopping, between them; and/or any other communication method generated/utilized by one or more of the system's components, and recognizable by the other components, for triggering a change in frequency. According to some embodiments, multiple frequencies may be simultaneously used, or used in parallel, by at least some of the transmitting beacon components.

In FIG. 7A, there is shown a schematic drawing of an exemplary system/module for radio frequency (RF) based object localization, in accordance with some embodiments: the system includes a management/control unit and three beacon components layout, wherein all units/components transmit and receive at a frequency of 800 MHz, as part of a first step of a signal transmission and reception scheme of one frequency at a time. The system, shown in FIG. 1A and in at least some of the following figures provided, including components and configuration thereof is an exemplary one. Various details depicted in the figures may be altered while retaining the functionalities and abilities of the disclosed system. For example, the number of system beacon components may be three—as exemplified, or may be higher, while still retaining and optionally improving, system functionality and abilities.

Figure 7B:
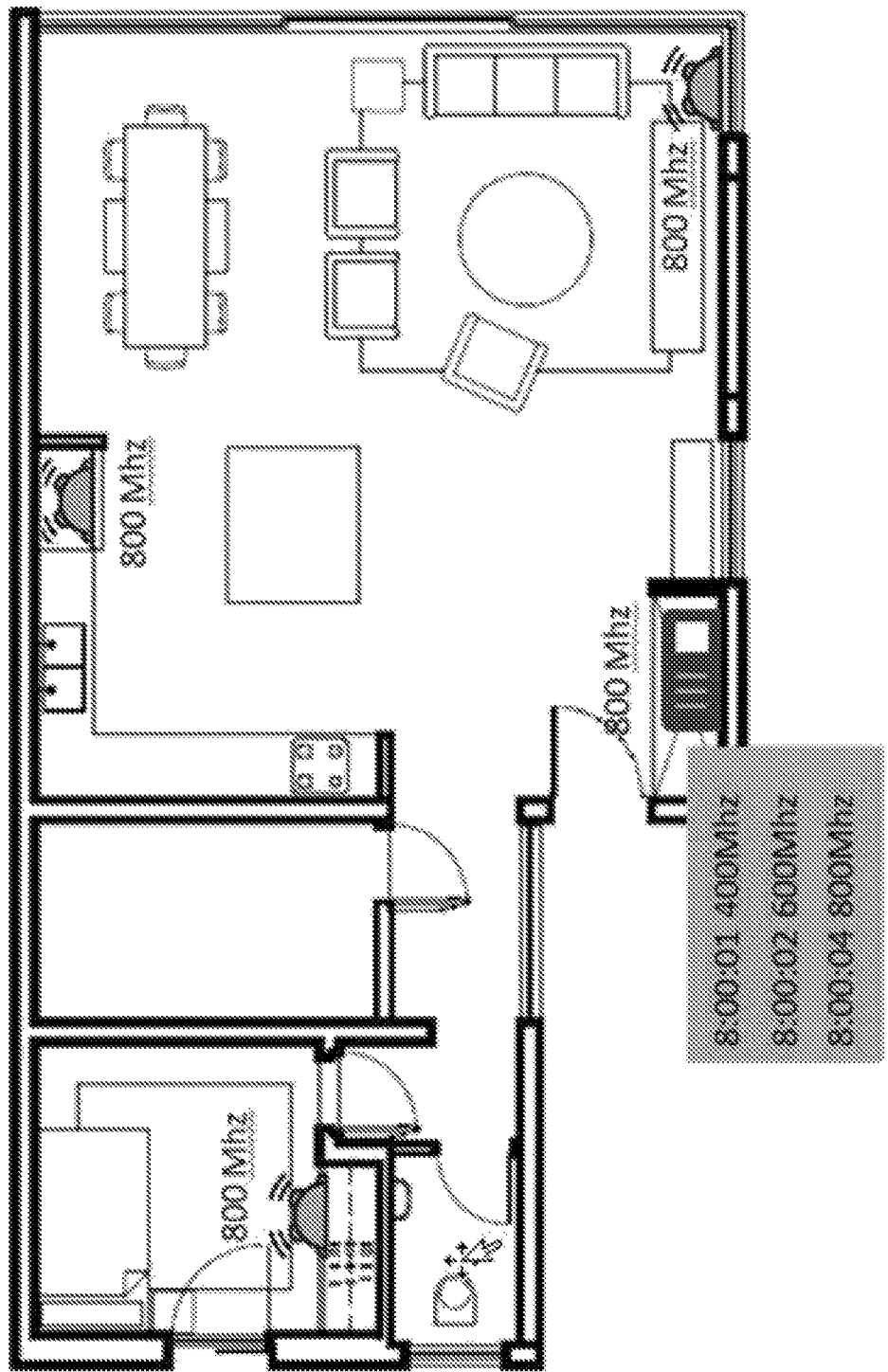
FIG. 7B is a schematic drawing of an exemplary system/module for radio frequency (RF) based object localization, in accordance with some embodiments of the present invention.

In FIG. 7B, there is shown a schematic drawing of an exemplary system/module for radio frequency (RF) based object localization, in accordance with some embodiments: the system includes a management/control unit and three beacon components layout, wherein the management/control unit issues a frequencies plan schedule, as part of a second step of a signal transmission and reception scheme of one frequency at a time.

In FIG. 7C, there is shown a schematic drawing of an exemplary system/module for radio frequency (RF) based object localization, in accordance with some embodiments: the system includes a management/control unit and three beacon components layout, wherein the frequencies plan is being distributed to the different beacons, as part of a third step of a signal transmission and reception scheme of one frequency at a time.

Figure 7D:
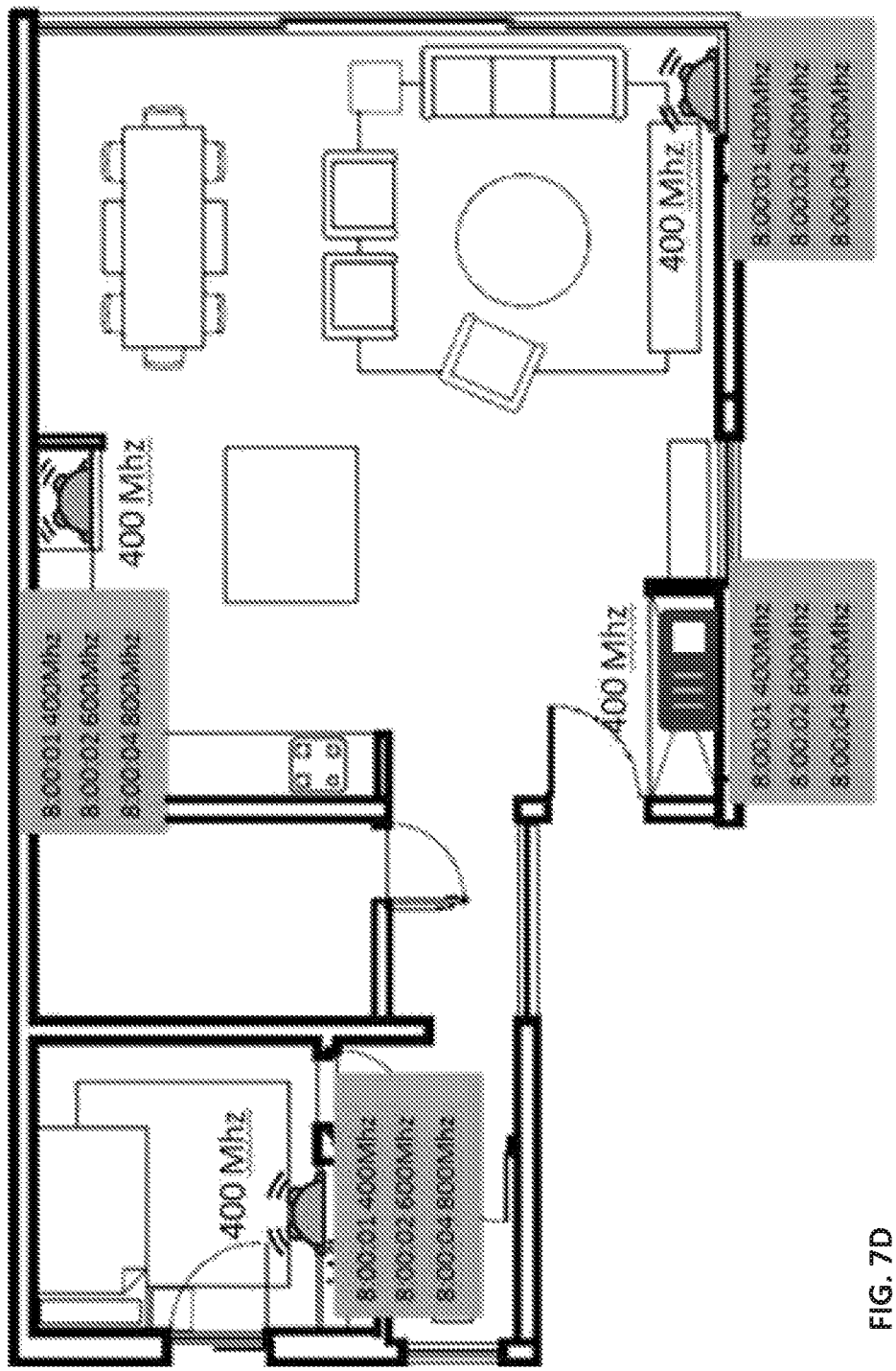
FIG. 7D is a schematic drawing of an exemplary system/module for radio frequency (RF) based object localization, in accordance with some embodiments of the present invention.

In FIG. 7D, there is shown a schematic drawing of an exemplary system/module for radio frequency (RF) based object localization, in accordance with some embodiments; the system includes a management/control unit and three beacon components layout, wherein at the designated time in the frequencies plan, all beacons change their frequency to 400 MHz concurrently, as part of a fourth step of a signal transmission and reception scheme of one frequency at a time.

Figure 7E:
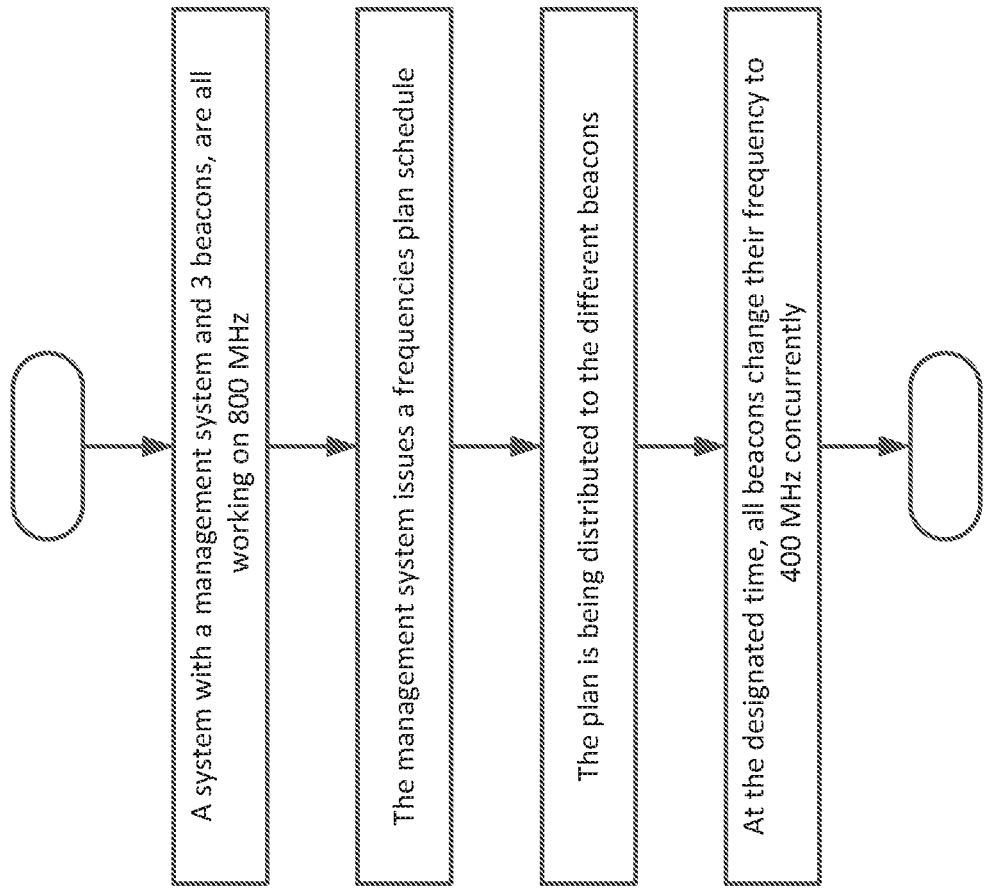
FIG. 7E is a flowchart of the main steps taken as part of a process for radio frequency (RF) based object localization, in accordance with some embodiments of the present invention.

In FIG. 7E, there is shown a flowchart of the main steps taken as part of a process for radio frequency (RF) based object localization, in accordance with some embodiments, wherein signal transmission and reception is performed one frequency at a time.

According to some embodiments, the frequencies plan schedule may be issued by the management system; and/or, may be preconfigured, thus rendering communication between the beacons and/or the management system unnecessary.

According to some embodiments, the beacons may transmit and receive signals in parallel in several frequencies, wherein the several frequencies may include one or more of the frequencies utilized by the system. For example, if covering/utilizing 3 different frequencies, system receivers and transmitters may receive and transmit signals on these 3 frequencies—substantially constantly and/or in parallel.

Figure 8:
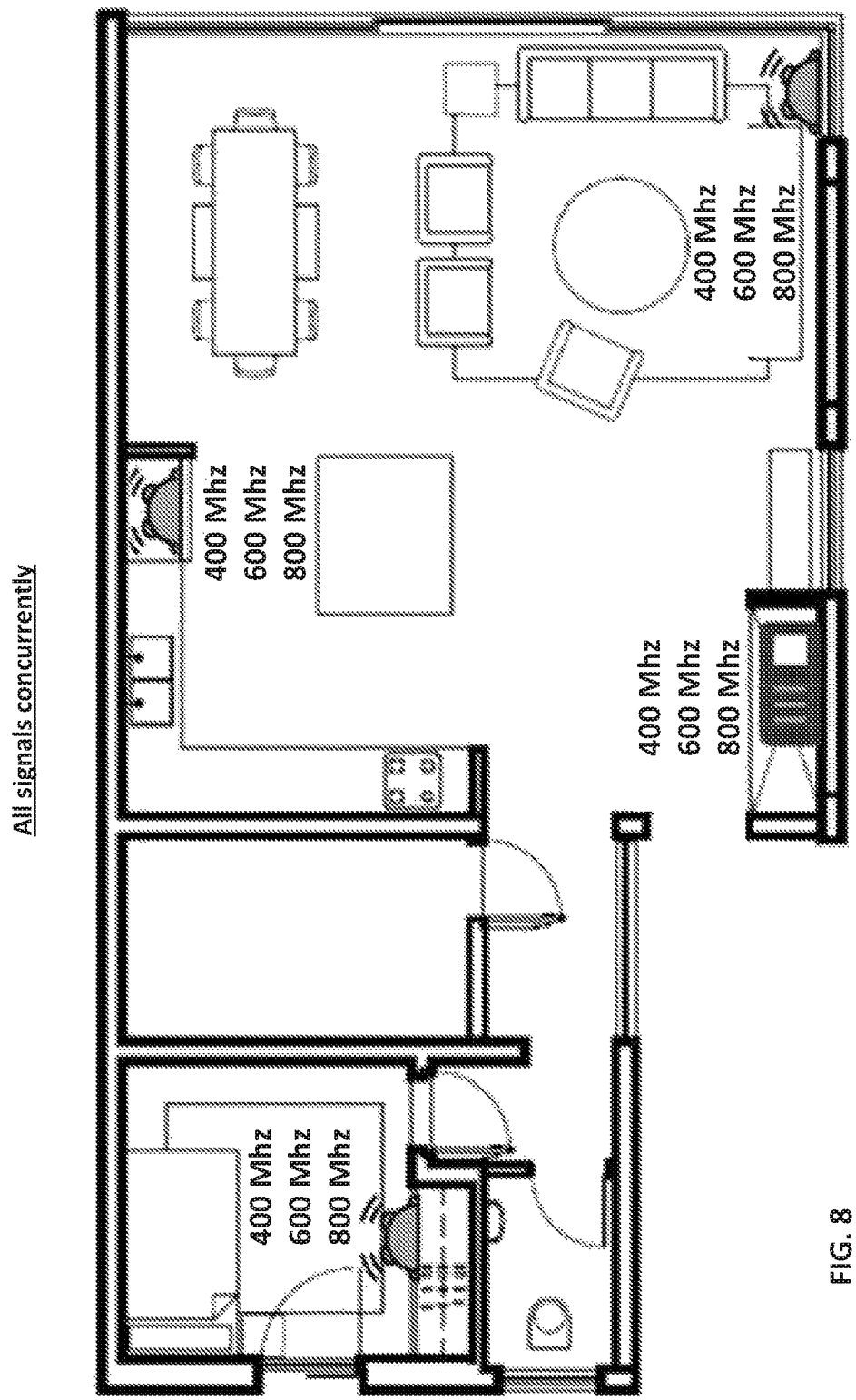
FIG. 8 is a schematic drawing of an exemplary system/module for radio frequency (RF) based object localization, in accordance with some embodiments of the present invention.

In FIG. 8, there is shown a schematic drawing of an exemplary system/module for radio frequency (RF) based object localization, in accordance with some embodiments; the system includes a management/control unit and three beacon components layout, wherein all units/components transmit and receive signals at multiple frequencies concurrently.

According to some embodiments, based on the characteristics of the different frequency signals, as received by a given dynamic component, a multi-layer signal-strength (or any other signals' parameter/s) levels map for the given dynamic component may be generated, wherein a separate layer in the map represents the signal parameters (e.g. signal strength) for each of the different signal frequencies or frequencies ranges, as received by the dynamic component.

Figure 9A:
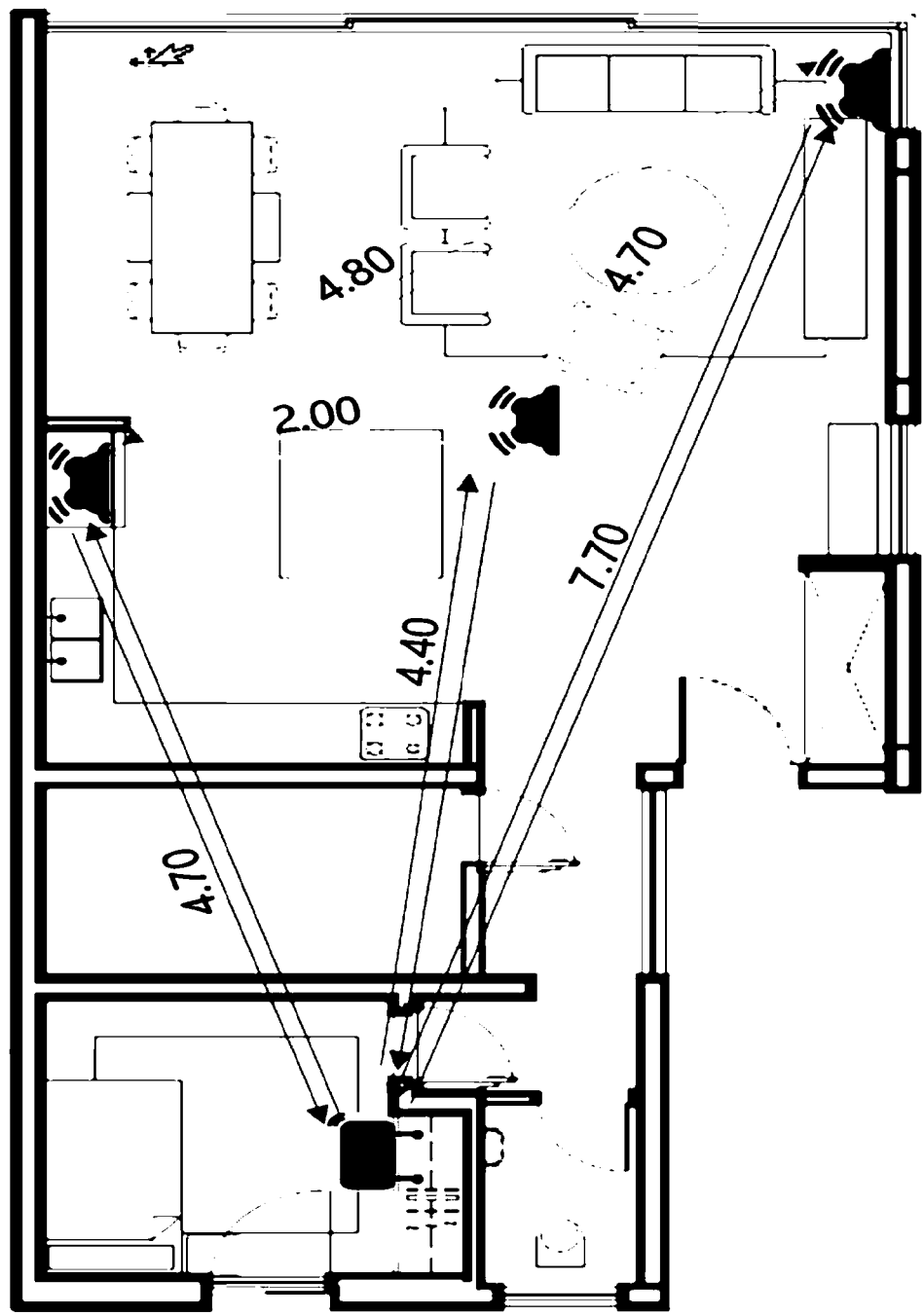
FIG. 9A is a schematic drawing of an exemplar system/module environment with three beacons/agents and one component (cart) that needs to be localized using multiple frequencies, in accordance with some embodiments of the present invention.

In FIG. 9A, there is shown a schematic drawing of an exemplary system/module environment with three beacons/agents and one component (cart) that needs to be localized using multiple frequencies, in accordance with some embodiments, wherein the numbers about each arrow represent the predicted distances in meters, based on an interpolation on the raw data (signal strength) collected.

Figure 9B:
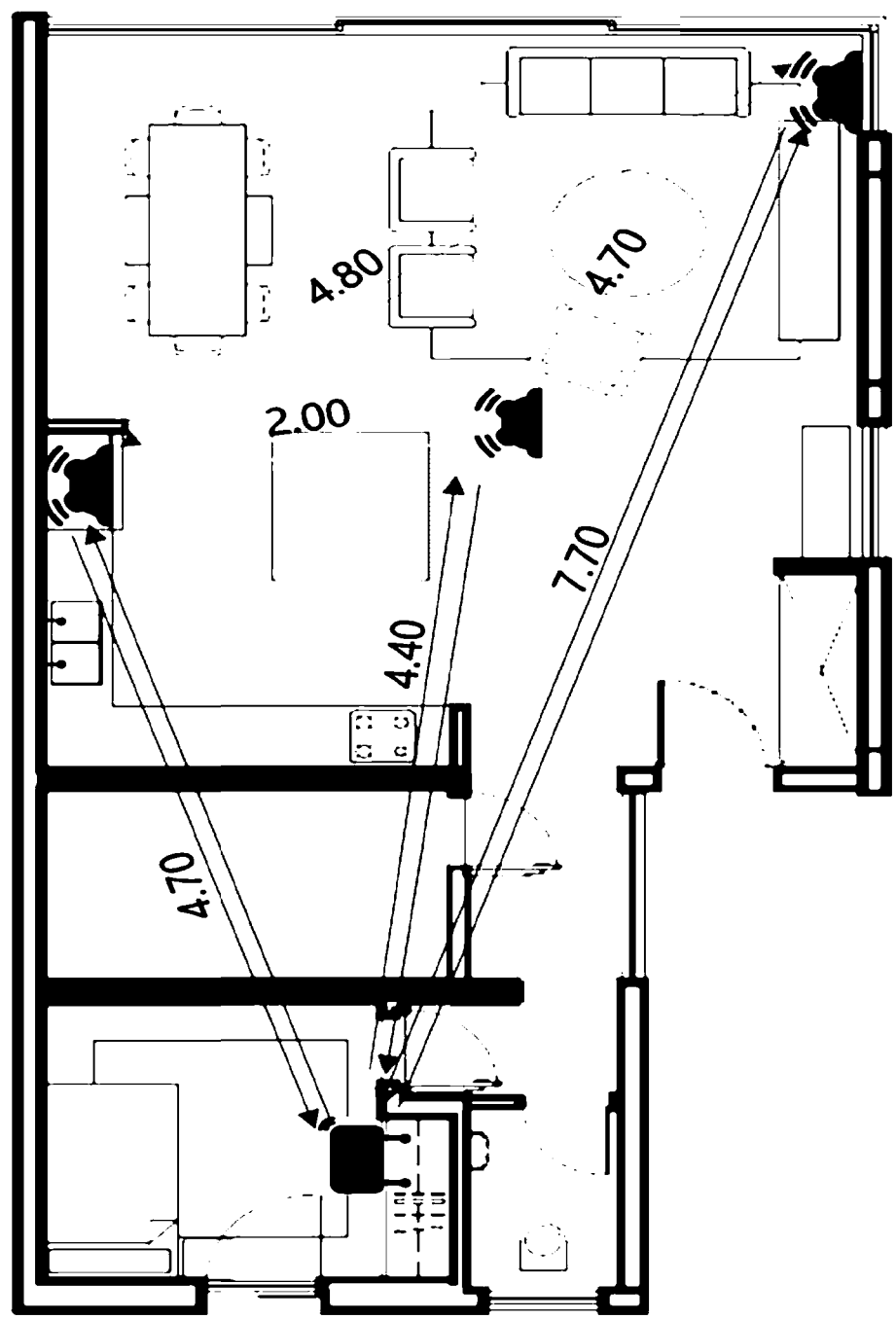
FIG. 9B is a schematic drawing of an exemplary system/module environment with three beacons/agents and one component (cart) that needs to be localized using multiple frequencies, in accordance with some embodiments of the present invention.

In FIG. 9B, there is shown a schematic drawing of an exemplary system/module environment with three beacons/agents and one component (cart) that needs to be localized using multiple frequencies, in accordance with some embodiments, wherein between some of the beacons/components pairs there are no line of sights due to the walls (highlighted) in the environment acting as obstacles and causing signals between corresponding beacons/component pairs to be weaker.

Figure 9C:
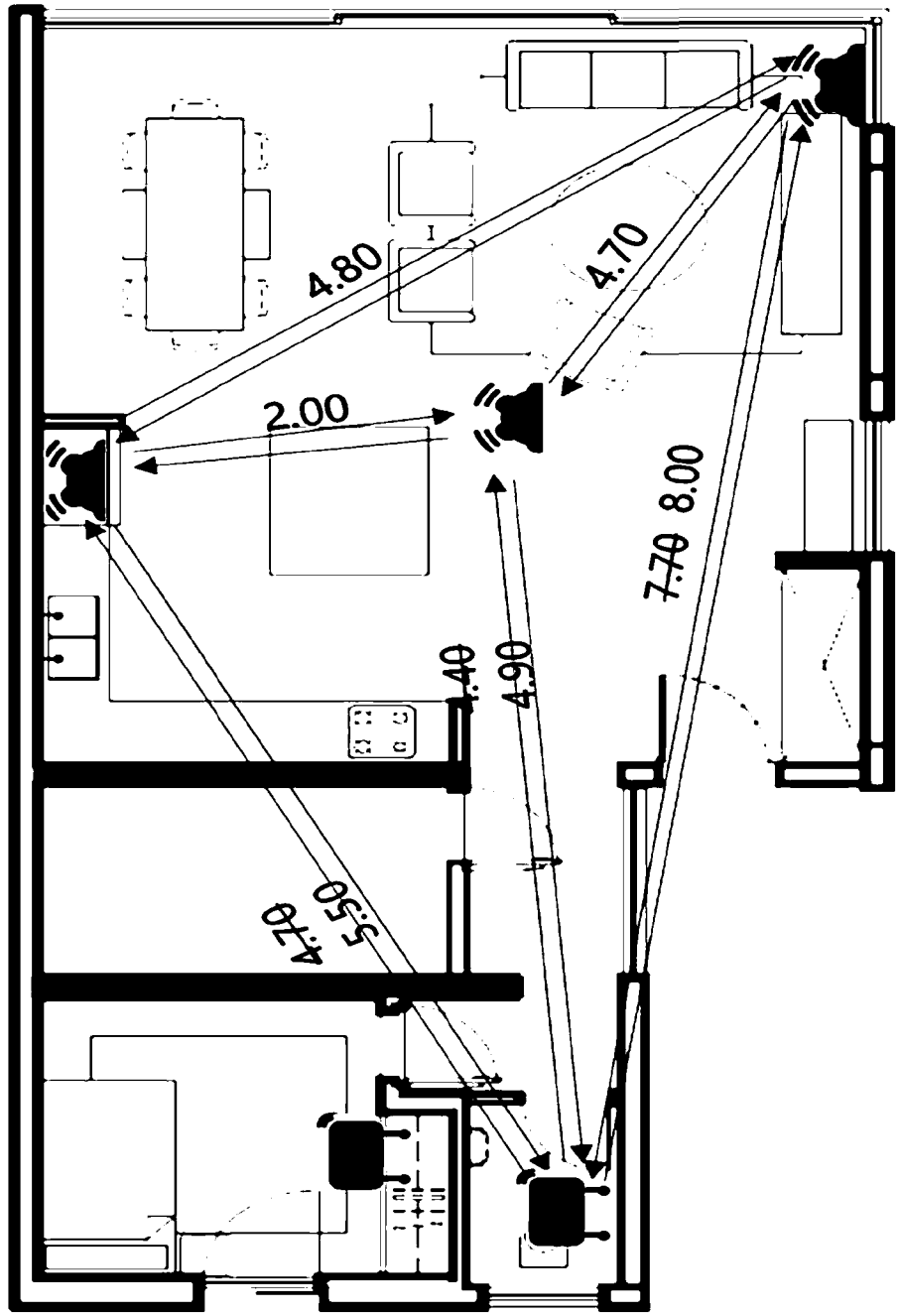
FIG. 9C is a schematic drawing of an exemplary system/module environment with three beacons/agents and one component (cart) that needs to be localized using multiple frequencies, in accordance with some embodiments of the present invention.

In FIG. 9C, there is shown a schematic drawing of an exemplary system/module environment with three beacons/agents and one component (cart) that needs to be localized using multiple frequencies, in accordance with some embodiments, wherein a calculation of the cart location based on only a first frequency is estimated to be wrong, as the signals strengths between some of the components pairs are weaker.

Figure 9D:
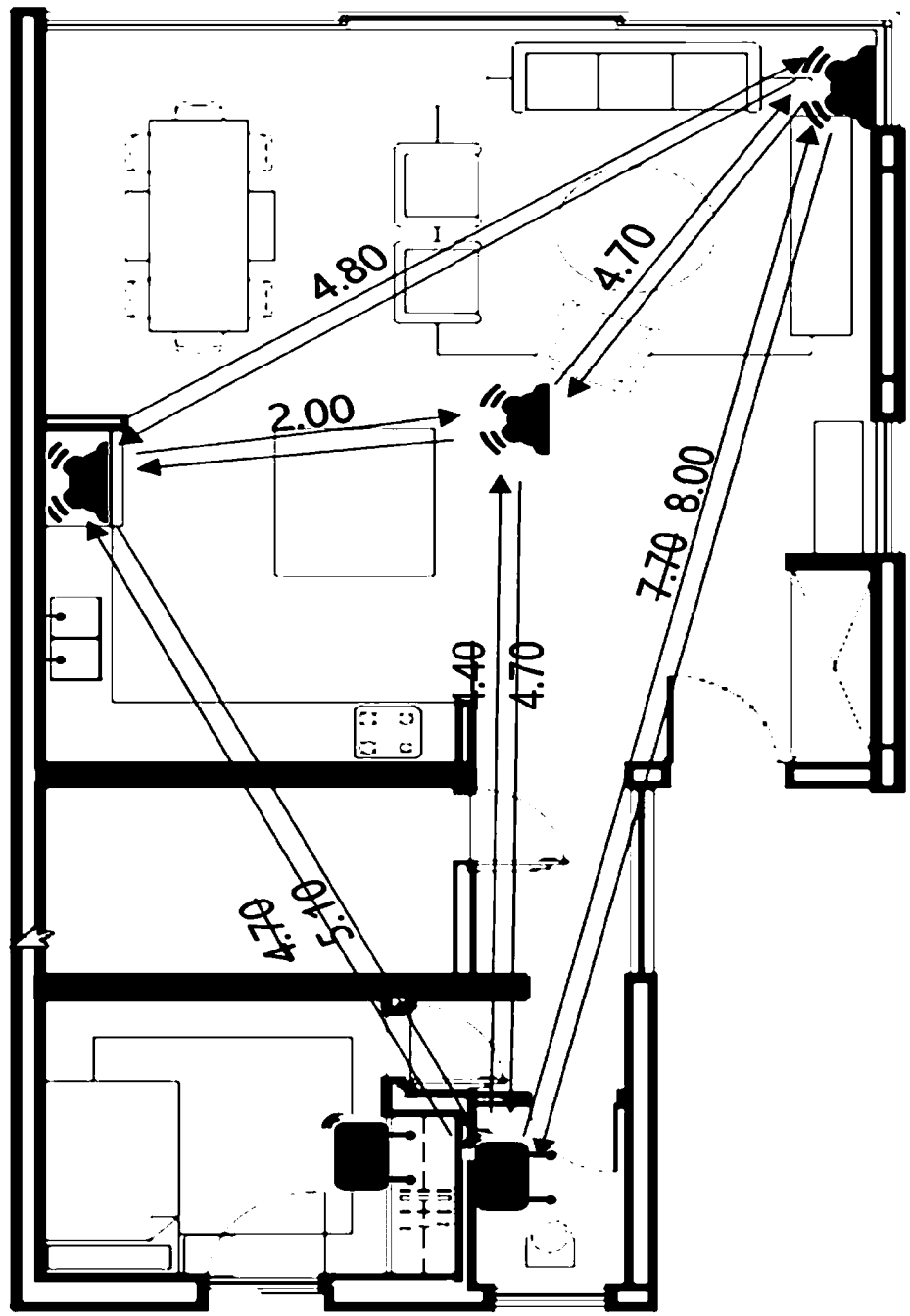
FIG. 9D is a schematic drawing of an exemplary system/module environment with three beacons/agents and one component (cart) that needs to be localized using multiple frequencies, in accordance with some embodiments of the present invention.

In FIG. 9D, there is shown a schematic drawing of an exemplary system/module environment with three beacons/agents and one component (cart) that needs to be localized using multiple frequencies, in accordance with some embodiments, wherein a calculation of the cart location based on a second frequency is shown to differently estimate the cart location, due to the frequency's different behavioral characteristics.

Figure 9E:
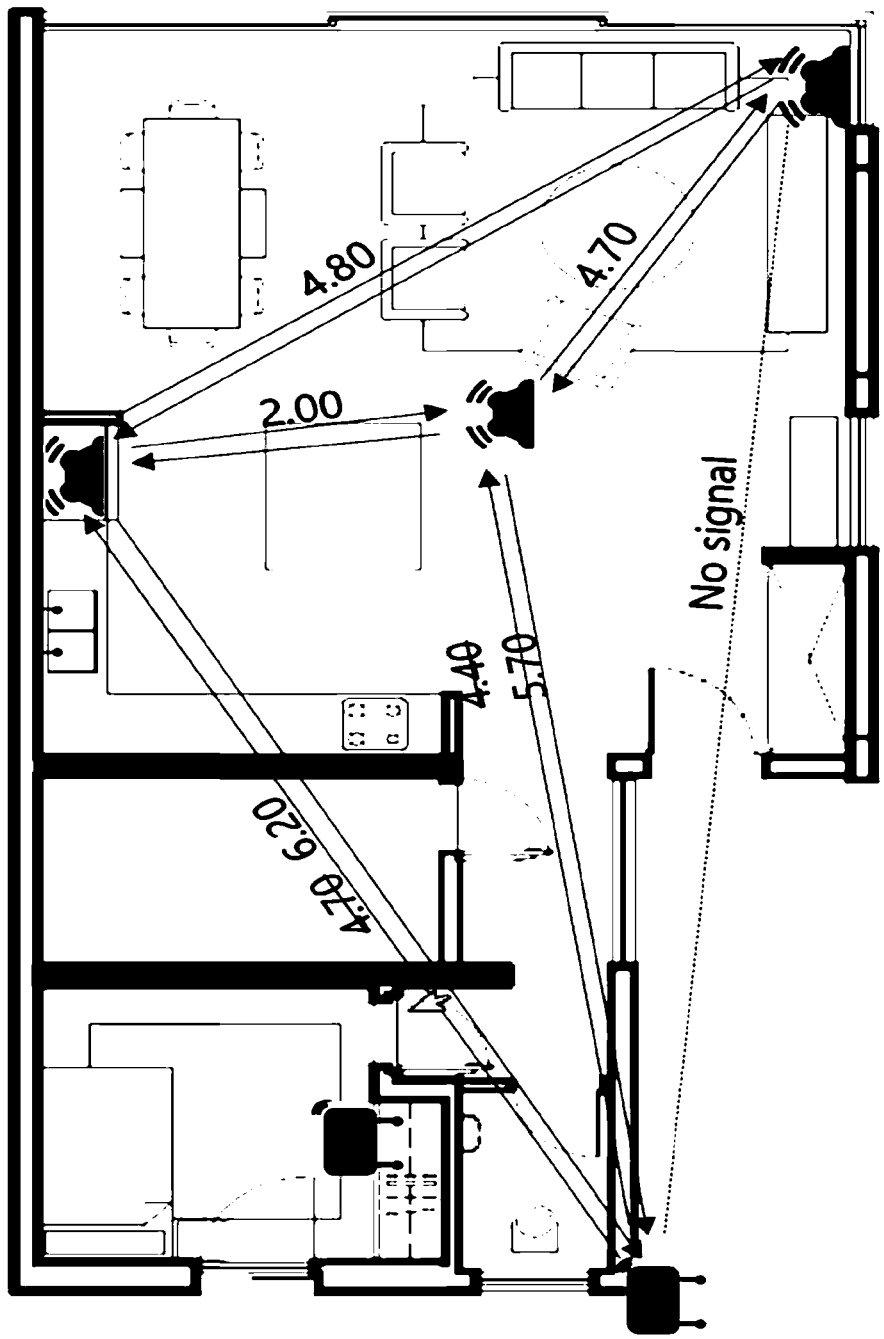
FIG. 9E is a schematic drawing of an exemplary system/module environment with three beacons/agents and one component (cart) that needs to be localized using multiple frequencies, in accordance with some embodiments of the present invention.

In FIG. 9E, there is shown a schematic drawing of an exemplary system/module environment with three beacons/agents and one component (cart) that needs to be localized using multiple frequencies, in accordance with some embodiments, wherein a calculation of the cart location based on a third frequency is shown to yet differently estimate the cart location, due to the frequency's different behavioral characteristics.

According to some embodiments, the location(s) of a given dynamic component within the space or the environment may be separately estimated—utilizing any known localization technique(s) (e.g. triangulation, fingerprinting) or combination of such—for each of the different frequency level layers in the map.

Figure 9F:
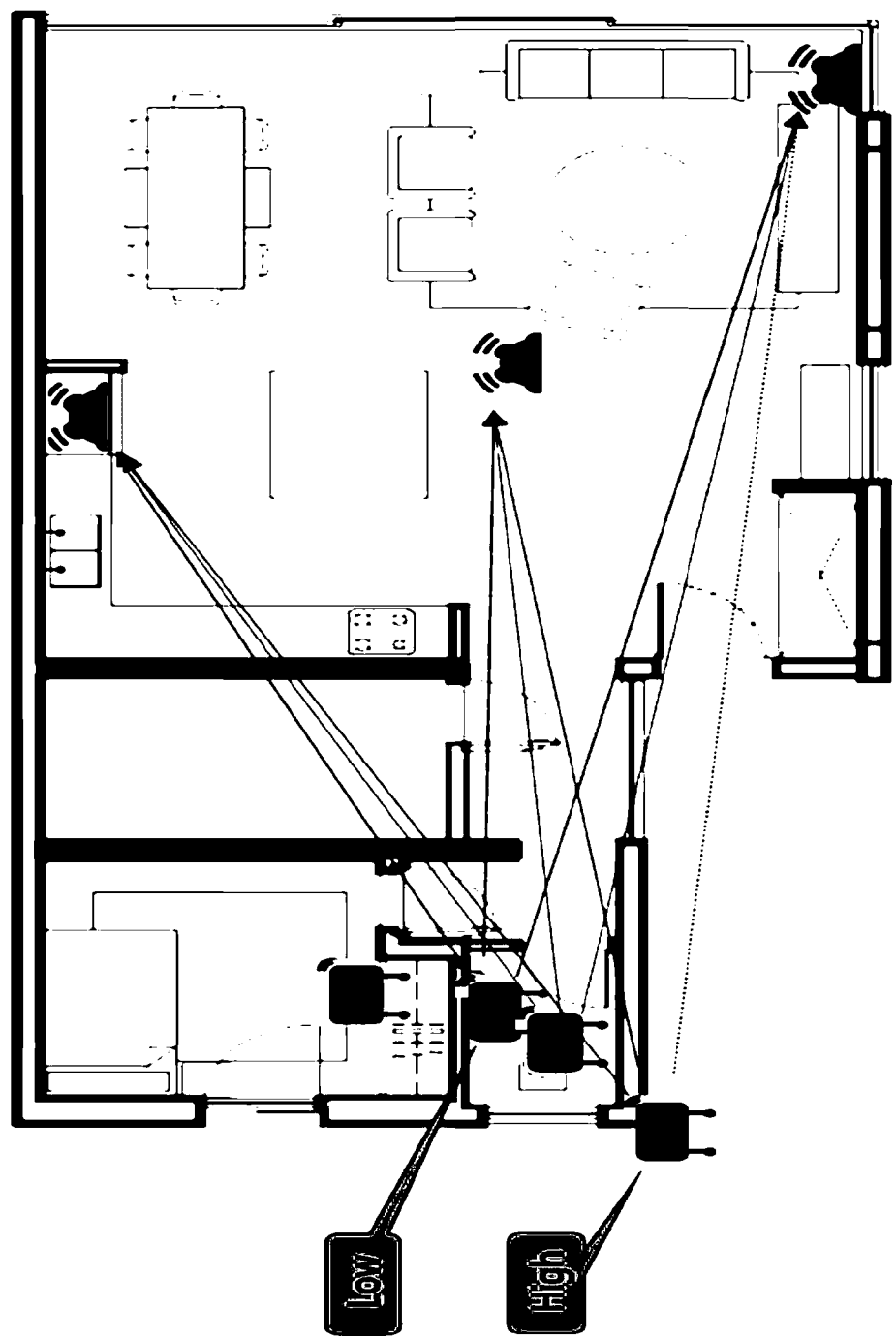
FIG. 9F is a schematic drawing of an exemplary system/module environment with three beacons/agents and one component (cart) that needs to be localized using multiple frequencies, in accordance with some embodiments of the present invention.

In FIG. 9F, there is shown a schematic drawing of an exemplary system/module environment with three beacons/agents and one component (cart) that needs to be localized using multiple frequencies, in accordance with some embodiments, wherein different location estimations for the cart—each based on a different frequency—are collectively overlaid over the same system environment.

According to some embodiments, as part of a map layers unification process, while considering the relative inherent advantages and disadvantages of each of the frequencies of the map's layers (e.g. the accuracy of higher frequencies and the penetration-ability/range of lower frequencies), the estimated dimensions, orientation and/or characteristics of obstacles and objects within the space or environment may be extrapolated.

Figure 9G:
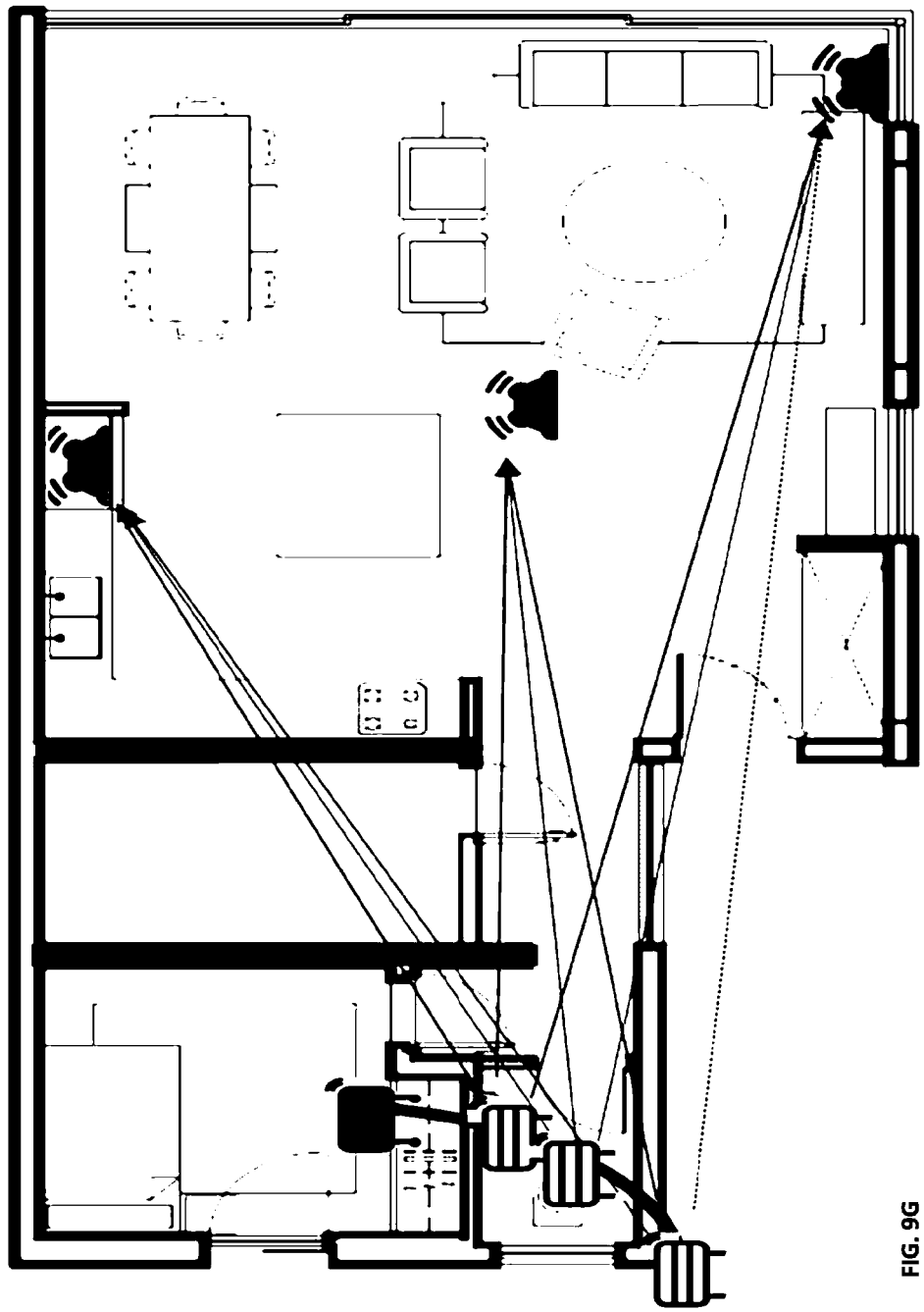
FIG. 9G is a schematic drawing of an exemplary system/module environment with three beacons/agents and one component (cart) that needs to be localized using multiple frequencies, in accordance with some embodiments of the present invention.

In FIG. 9G, there is shown a schematic drawing of an exemplary system/module environment with three beacons/agents and one component (cart) that needs to be localized using multiple frequencies, in accordance with some embodiments, wherein based on the known nature of the waves (frequencies) of each sample, the implied: errors, noise and diversions/deviations/divergences of each of the utilized frequencies is inferred, enabling an improved localization of the cart.

According to some embodiments, obstacle and object characteristics, may be further analyzed to learn about the electromagnetic pattern in the space or environment—based on which, further analysis and enhancement of the map may be performed. The process may be iterated to gradually accumulate knowledge about the space/environment and its physical and electromagnetic characteristics and spatial layout. These, in turn, may be utilized for more accurate RF based localization, of the dynamic components therein.

Figure 9H:
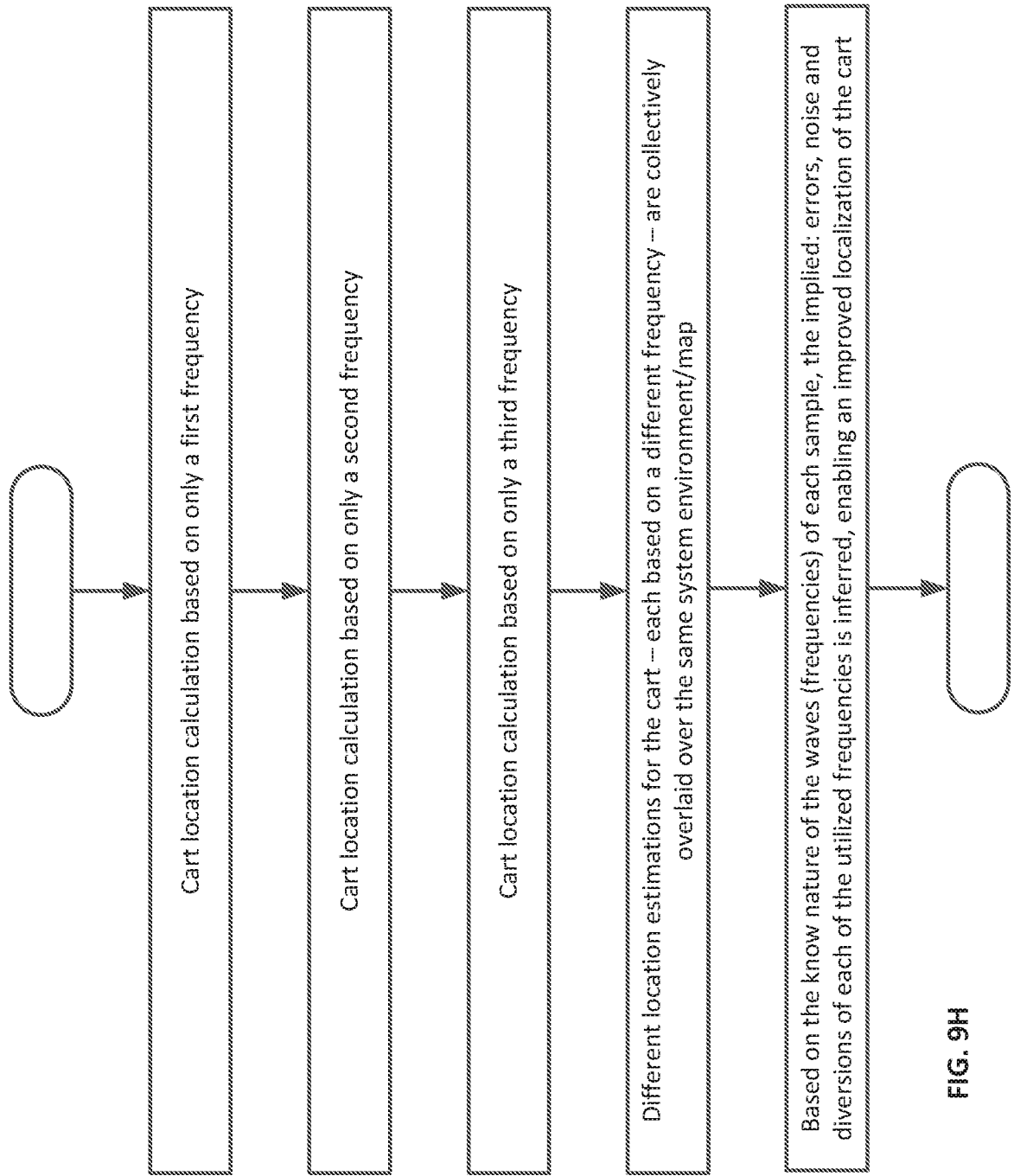
FIG. 9H is a flowchart of the main steps taken as part of a process for radio frequency (RF) based object localization, in accordance with some embodiments of the present invention.

In FIG. 9H, there is shown a flowchart of the main steps taken as part of a process for radio frequency (RF) based object localization, in accordance with some embodiments, wherein a component is localized using multiple frequencies.

Medical Items Storage Indication Module

According to some embodiments, there may be provided a medical items storage indication system, the medical items storage indication system may be implemented as a separate/independent/stand-alone system; or, may be implemented as a medical item storage indication module, included in a medical treatment procedure tracking, evaluation and facilitation/assistance/support system, in accordance with embodiments of the present invention—wherein medical items storage indication capabilities may be triggered as part of the issuance of commands/requests to medical procedure related machines and devices, made by a medical device commanding module in accordance with some embodiments.

According to some embodiments, there may be provided a medical equipment storage device that carries different medical items. These items may be stored in different locations inside the medical equipment storage device, such as on top of the storage device, in drawers, in shelves, inside dedicated trays within the drawers or the shelves, or in any additional location in, on or near the medical equipment storage device.

A medical item storage indication system/module, in accordance with some embodiments, may indicate one or more specific parts, drawers, shelves, trays, compartments, boxes, or the like—within the medical equipment storage device. The position of items within the medical equipment storage device may be based on: one or more received medical item identifiers, of medical items related to the medical procedure being carried out or to a specific stage of the procedure being executed; and a reference table or map correlating medical item identifiers to their arrangement positions/places within the medical equipment storage device.

A system/module in accordance with some embodiments, may include (1) an Item Identifier Receipt Interface for receiving a medical item identification (e.g. item name, item number or any other identifier of the item); (2) an Item Location Retrieval Logic or Processor for identifying the location of the item for which identification was received; and (3) an Item Location Indication Logic or Processor and one or more Indication Components or marker devices for marking, indicating and/or providing better accessibility to the required item.

According to some embodiments, the Item Identifier Receipt Interface may receive the item identification data from a user, for example a medical staff member. The user may utilize a Medical Items Selection Interface that may take the form of a customized hardware and/or software interface allowing for the selection of items and/or a standard input device, such as a keyboard, a button, a speech identification device, or the like.

According to some embodiments, the Item Identifier Receipt Interface may receive the item identification data from a Medical Procedure Monitoring System. The Medical Procedure Monitoring System may utilize data from one or more microphones, cameras, sensors and/or interfaced medical devices—for identifying a medical procedure being carried out and/or specifics thereof, such as: specific stages of the procedure, medical staff members involved, patient medical records and the like. Based on the identified medical procedure and details thereof, requirements for specific medical equipment/item(s) at specific times along the procedure may be derived. These requirements may be translated into identifiers of the specific medical equipment/items needed and relayed to the Item Identifier Receipt Interface of the medical equipment storage device for their indication to the medical staff members.

According to some embodiments, the Item Location Retrieval Logic may receive the identification data of the item from the Medical Items Selection Interface and using a reference table (e.g. an indexed table), lookup the item and identify its location on the storage device, inside the storage device, or at the proximity of the storage device.

According to some embodiments, the Item Location Indication Logic and one or more Indication Components may indicate the location of the selected item(s), or provide better accessibility to it/them. Indicating the location of an item may be done using any marker device or indicator, providing vocal, visual and/or other indication about the location of the item within/on/near the storage device.

According to some embodiments, the Indication Components may take the form of: a light source (e.g. LED), at the relevant location (e.g. on top of, on bottom of, on front of, beneath, above and/or inside a drawer of the storage device), that is turned on: a sound source (e.g. speaker/buzzer), at the relevant location, that is turned on; a vibrating unit (e.g. vibrating motor), at the relevant location, that is turned on; and/or any other form of indicating component that may guide, or draw the attention of, a medical staff member to the required medical item(s). An item indication, in accordance with some embodiments, may take the form of a constant signal (e.g. continuous light), a breaking signal (e.g. a blinking light), a strengthening or weakening signal (e.g. a light getting brighter and brighter), a changing signal (e.g. a light gradually changing the color of its emitted light) and/or any combination of the above.

According to some embodiments, the Indication Components may provide better accessibility to the required medical item by physical gestures, for example, withdrawing or extracting the item out of the storage device, opening the relevant drawer or compartment of the storage device and/or the like.

According to some embodiments, multiple Indication Components of the storage device may simultaneously indicate multiple stored items. Accordingly, the position of different items may be differently indicated, thus differentiating: (1) the types of the indicated items—for example: mechanical chisels and clamps, electric items and devices, chemical substances and drugs; (2) the use order of the indicated item—for example: item needed now, next item to be needed; and/or (3) the type of staff member associated with the indicated item—for example: items for a surgeon, items for an anesthesiologist, items for a nurse.

According to some embodiments, the multiple Indication Components may differentiate between multiple types of stored items by outputting a different indication or signal type, for each item type. For example: mechanical chisels and clamps may be indicated by a green light, electric items and devices by blue and chemical substances and drugs by red; an item needed now may be indicated by a constant light, next item to be needed by a fast blinking light and the next following item to be needed by a slow blinking light; and/or (3) an item needed by a doctor may be indicated by a light and a beep, an item for an anesthesiologist may be indicated by a light and a buzz and an item for a nurse may be indicated by light only.

Figure 10:
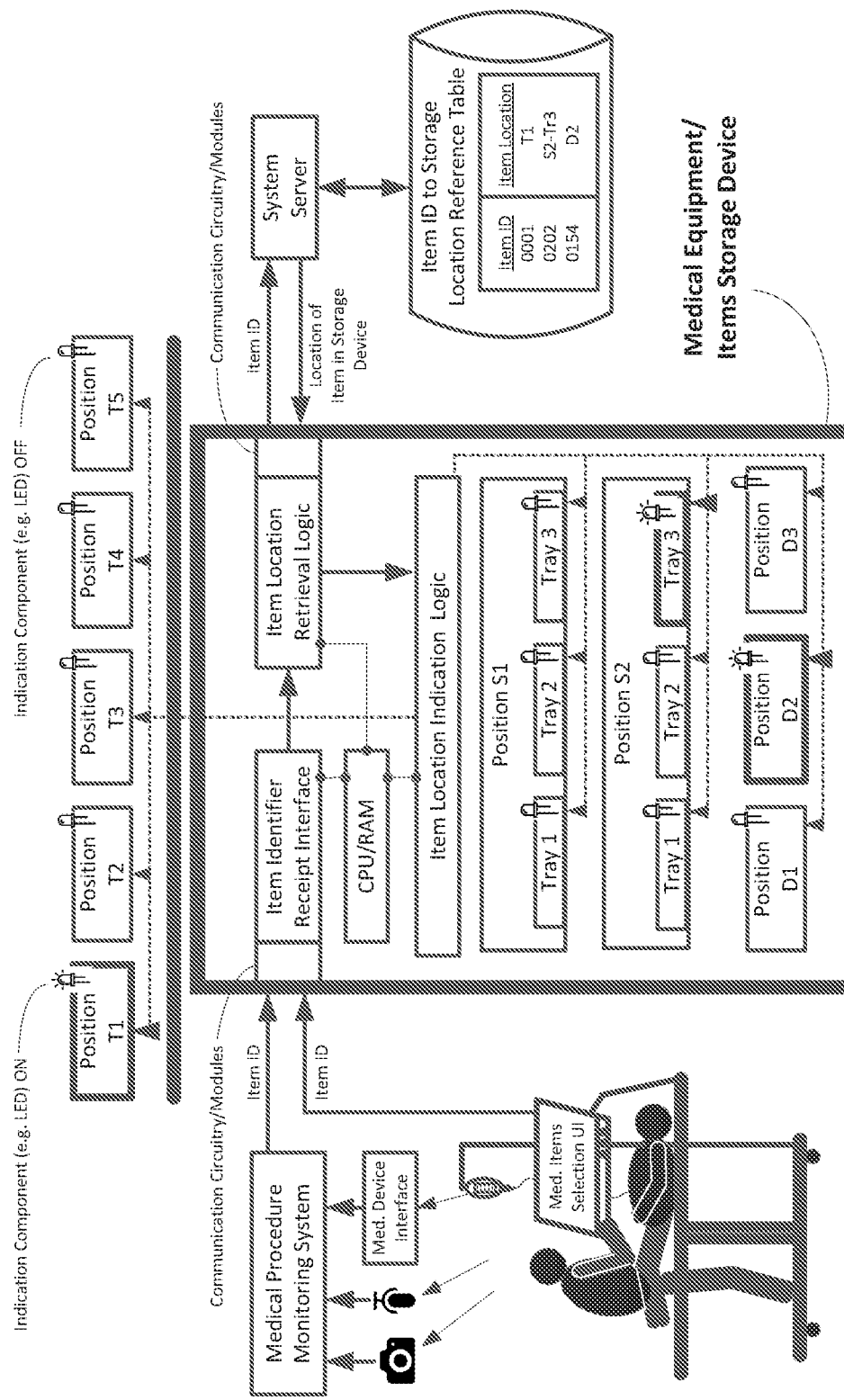
FIG. 10 is a block diagram of an exemplary system/module for self-indicated medical equipment storage, in accordance with some embodiments of the present invention.

In FIG. 10, there is shown a block diagram of an exemplary system/module for self-indicated medical equipment storage, in accordance with some embodiments of the present invention. In the figure, there is shown an exemplary medical equipment storage device, including the following storage places/positions: top positions (T1-T5); drawer positions (D1-D3); shelf positions (S1-S2); and tray positions (Tray1-Tray3), within each of shelf positions. Each of the positions includes a respective indication component. The exemplary medical equipment storage device shown, further includes a Central Processing Unit (CPU) for managing and controlling the operation of the interfaces and logics of the storage device and Random Access Memory (RAM) for data storage/registry as part of its operation. Further shown are communication circuitries/modules of the device.

Identifiers of medical items (Item ID) stored in the storage device, are received by the storage device's Item Identifier Receipt Interface from: the shown Medical Items Selection User-Interface—based on direct requests inputted by a medical staff member, and/or from the shown Medical Procedure Monitoring System—based on medical procedure related data collected through the shown sensors (camera, microphone) and Medical Device Interface of the monitoring system, wherein the medical procedure related data, or parts/derivations thereof, are indicative of medical stored items/equipment required for the medical procedure being carried out.

The identifiers of medical items (Item ID) required for the procedure, or a specific stage thereof, are relayed to the Item Location Retrieval Logic that uses the identifiers for referencing the shown Item Identifier to Storage Location Reference Table—retrieving the item locations, within the storage device, corresponding to the identifiers used. The database including the Storage Location Reference Table may be a local database integrated into the Medical Equipment Storage Device and/or a remote database functionally associated/networked with the Medical Equipment Storage Device, possibly through the shown system server.

Upon retrieval of the locations of the required medical item(s) within the storage device, the locations are relayed to the Item Location Indication Logic shown. The Item Location Indication Logic then sends indication commands to indication component(s), of the medical equipment storage device, corresponding to the retrieved item locations. In the example shown, item identifiers: 0001, 0202 and 0154, are received by the storage device. Corresponding item positions/locations: T1, S2-Tr3 and D2 (Top1, Shelf1-Tray3 and Drawer2, respectively), are retrieved from the reference table and indication commands are sent to the indication component(s) at these storage device positions/locations. Indication components positions/locations: T, S2-Tr3 and D2, are accordingly shown to be turned ON—pointed to by larger arrow heads in the figure and shown to emit a position indicative light signal.

Figure 11:
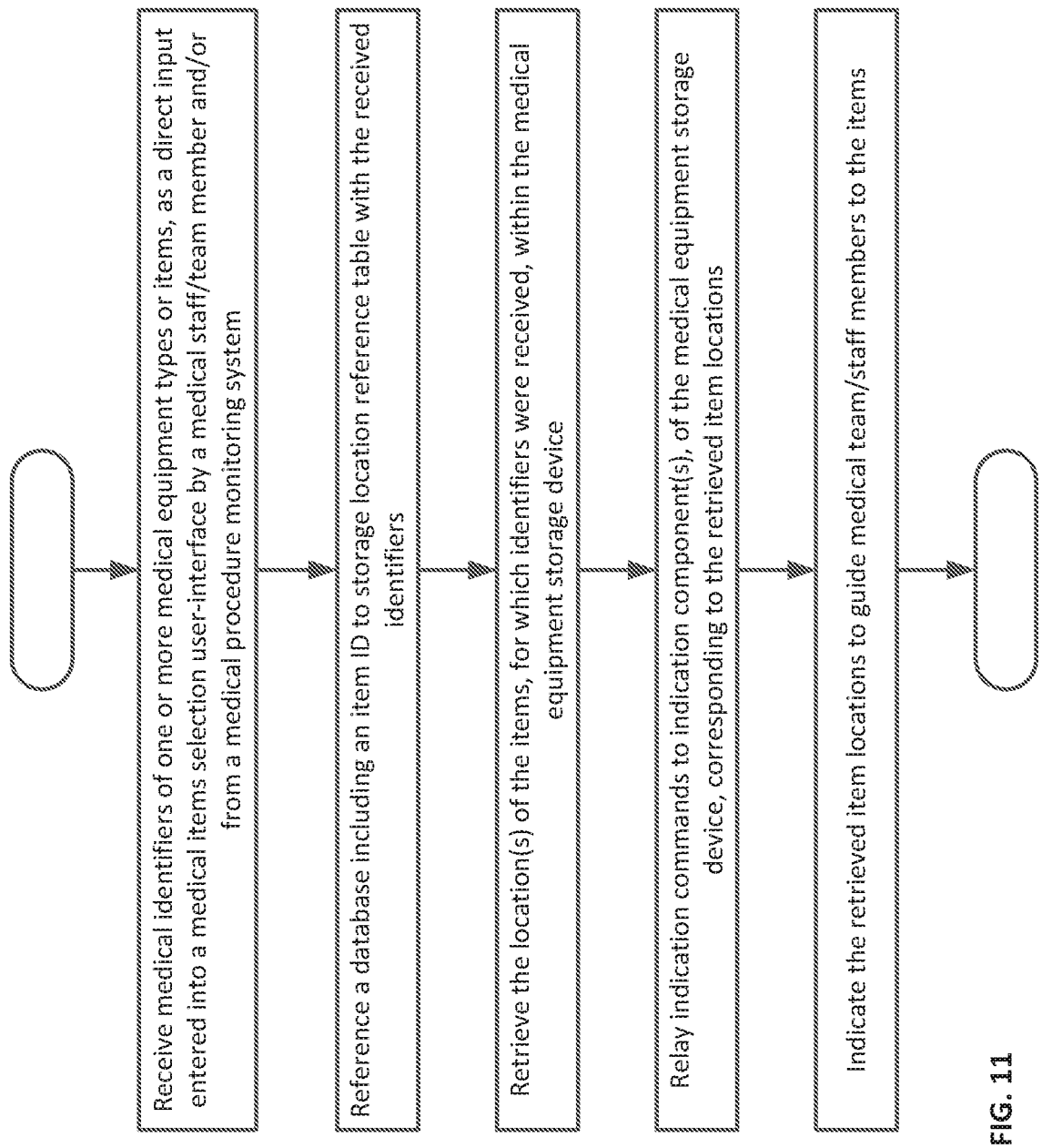
FIG. 11 is a flowchart of the main steps executed by an exemplary system/module for self-indicated medical equipment storage, in accordance with some embodiments of the present invention.

In FIG. 11, there is shown a flowchart of the main steps executed by an exemplary system/module for self-indicated medical equipment storage, in accordance with some embodiments of the present invention. Shown steps include: (1) Receive medical identifiers of one or more medical equipment types or items, as a direct input entered into a medical items selection user-interface by a medical staff/team member and/or from a medical procedure monitoring system; (2) Reference a database including an item ID to storage location reference table with the received identifiers; (3) Retrieve the location(s) of the items, for which identifiers were received, within the medical equipment storage device; (4) Relay indication commands to indication component(s), of the medical equipment storage device, corresponding to the retrieved item locations; and (5) Indicate the retrieved item locations to guide medical team/staff members to them.

Figure 12A:
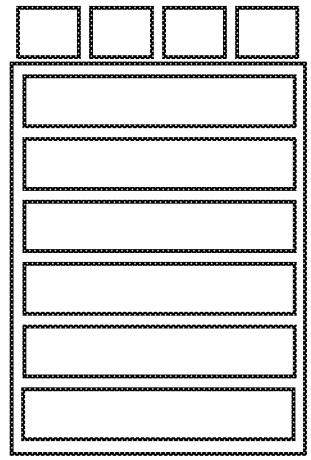
FIG. 12A is a schematic drawing of an exemplary storage layout of a system/module for self-indicated medical equipment storage, in accordance with some embodiments of the present invention.

In FIG. 12A, there is shown a schematic drawing of an exemplary storage layout of a system/module for self-indicated medical equipment storage, in accordance with some embodiments; wherein the system is deployed on a medical equipment storage device that, in this example, contains drawers, shelves, trays and storage on top of the storage device.

Figure 12B:
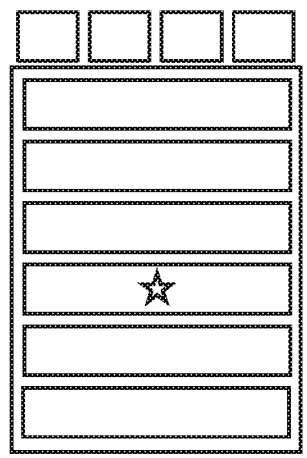
FIG. 12B is a schematic drawing of an exemplary storage layout of a system/module for self-indicated medical equipment storage, in accordance with some embodiments of the present invention.

In FIG. 12B, there is shown a schematic drawing of an exemplary storage layout of a system/module for self-indicated medical equipment storage, in accordance with some embodiments; wherein the system receives a command to locate a specific item, identifies the item to be inside the third drawer and turns on an indicator (e.g. a LED light) that is located on the drawer.

Figure 12C:
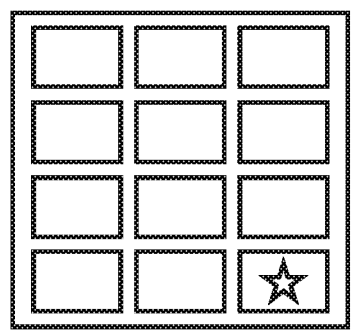
FIG. 12C is a schematic drawing of an exemplary storage layout of a system/module for self-indicated medical equipment storage, wherein a sketch of the arrangement within the third drawer of the medical equipment storage device is shown, in accordance with some embodiments of the present invention.

In FIG. 12C, there is shown a schematic drawing of an exemplary storage layout of a system/module for self-indicated medical equipment storage, wherein a sketch of the arrangement within the third drawer of the medical equipment storage device is shown, in accordance with some embodiments; the system received a command to locate a specific item, identified and indicated the item to be inside one of the trays of the third drawer and now indicates (e.g. by a LED light indication) the specific tray within the third drawer in which the required item is located.

Procedure Documentation Module

According to some embodiments of the present invention, the acquired, collected, analyzed and/or generated data, throughout the medical procedure, may be stored/saved for future retrieval and reference in a medical records repository.

According to some embodiments of the present invention, the system may record and store retrieved, acquired and/or processed/analyzed information about the tracked/monitored medical procedure. The data may be documented in connection with, or along with references/indicators/pointers/correlators to: the specific type of medical procedure, the specific medical procedure and/or specific step(s) of the medical procedure—which it was derived from. According to some embodiments, the data, or specific parts/sections thereof may be documented in connection with, or along with references/indicators/pointers/correlators to, other medical procedures types—at least partially relating to, or associated with, the actual medical procedure it was derived from.

Documented data types may, for example, be divided into the following types: (1) raw data, such as audio files, video files and raw medical indicators—this data may be stored for future inspection and verification purposes; (2) processed data, such as text (converted/transcribed from audio) and/or processing outputs of the image(s); and/or (3) electronic medical records (EMR) or electronic health records (EHR) that may be filled by the system in accordance with a corresponding (e.g. procedure type matching) digital template or form. Some or all of the data documented, may be used by the system as a source of data for the evaluation, analysis and support of later medical procedures tracked/monitored by the system.

According to some embodiments, updated medical procedure documentation may be utilized for medical procedure enhancement and/or optimization—wherein specific updates are designed to improve a medical procedure protocol to make it more efficient, effective and/or successful. Protocol enhancement/optimization updates may, for example, be selected based on: the frequency (e.g. over a given high frequency threshold number) of their reoccurrences within a specific medical procedure, the ratio between their number of reoccurrences within a specific medical procedure and the total of number of times the same specific medical procedure has be executed (e.g. over a given ratio threshold value); their occurrence within medical procedure(s) determined/tagged/designated as successful; and/or based on other medical procedure related criteria.

Procedure Simulation Module

According to some embodiments, medical procedure environment/setting tracking, monitoring, evaluating, analyzing and/or operation supporting, methodologies and modules as described herein, may be utilized for medical staff members' performance evaluation purposes. The performance of a medical staff member, or a group of medical staff members, may be assessed based on the monitoring and evaluation of his/their actions while participation/part-taking in the medical procedure—as described herein.

Medical procedure assistance as described herein, may be at least partially substituted with a procedure simulation module, measuring and logging the deviations/divergences and non-compliances, of monitored medical staff member(s), from a protocol of a medical procedure being performed/carried-out by them. Measured deviations/divergences may be mathematically and/or statistically processed to generate an evaluation index value (e.g. grade, rank, result, skill-level).

The procedure simulation module may accordingly evaluate the performance of medical staff member(s) participating in an actual/real monitored medical procedure and/or in a medical training simulation designed to train/improve staff members or examine/test their performance/skills.

Exemplary System Operation Scenario

The following, is an exemplary operation scenario of a system for medical procedure tracking, evaluation and facilitation/assistance/support, in accordance with some embodiments of the present invention.

In an in-hospital resuscitation procedure:

(1) A nurse identifies a resuscitation case—the patient has no pulse.

Potentially relevant data, received by the system from medical devices, includes: ECG—heart activity information; Defibrillator—executed and being executed Defibrillator actions taken and heart activity information (e.g. pulse and blood pressure); and bio-parameters/physiological-parameters Monitor: pulse, temperature, blood pressure, oxygen levels.

(2) The nurse initiates a resuscitation procedure, using a smart device she holds.

The device identifies its own location and therefore the resuscitation procedure's location, directs the emergency team to the location, and moves a crash-cart autonomously to its location. The locations, or the precision/accuracy of the locations (for example, instead of, or in addition to, GPS/Cellular based location) of the crash-cart, the smart-device/procedure/patient and the medical staff members—are determined or improved/optimized by multi frequency based positioning and navigation.

(3) The team starts a resuscitation process. Throughout the resuscitation, the system tracks the vocal communications, the voices, the noises and the ambient sounds, at the environment of the procedure. Data is continuously/intermittently received or retrieved from interfaced medical devices, the patient's medical records and additional inputs from the environment and from functionally associated devices and systems. Received inputs are analyzed by the system, to provide medical staff recommendations and indications; and to automatically generate medical procedure and patient records.

Potentially relevant data inputs, retrieved by the system from the patient's medical records, include: Allergies (e.g. an allergy to latex gloves that may indicate the medical team not to use gloves); Age (e.g. infant/child/adult)—may affect the resuscitation algorithm/protocol type; Weight—may affect resuscitation related medicine/drug dosages; and Other important medical history records that may raise concerns and/or alter/modify treatments.

Potentially relevant data inputs, acquired by the system from the environment, include: Noise from the resuscitation process, as the presses (circulation presses) noise that may indicate whether the staff perform the action and what is the frequency of the presses: Noise of medical devices, such as beeps of the monitor that may indicate pulse or electrical activity of the patient's heart, and Environment general information, such as the location of the procedure (monitored medical department for example).

The multiple system acquired/received data and information inputs, are analyzed using any combination of circuitry/software logics/algorithms, such as, but not limited to, data fusion algorithms and/or logics.

(4) When the system analyzes a request to use a specific drug or medical device, it assists the medical staff, by indicating the location of the specific medical device or drug on top of the repository/storage-unit in which the device or drug are stored—for example, on top of a crash-cart, using, for example, led lights that will direct to the location of the device or drug.

Exemplary, system provided resuscitation relevant recommendations/indications/notifications, given to medical staff member(s), include: 'You have initiated the resuscitation procedure 2 minutes ago, and an electric shock has NOT yet been provided—please give a shock ASAP'; 'Chest compressions being performed are too slow, please speed up their frequency'; 'It is time for drug therapy, please give patient 1 milligram of epinephrine'; 'The staff member command given was referred to a wrong dosage, please give 1 milligram of epinephrine'; and 'You have provided the drug therapy, but have not flushed'.

According to some embodiments of the present invention, a medical procedure tracking and assistance system, may comprise one or more video cameras, one or more acoustic sensors or one or more medical device interfaces for acquiring video, audio or medical device feeds from a medical treatment setting.

According to some embodiments, the system may comprise a scene evaluation module for detecting scene related features in the video, audio or medical device feeds from the medical treatment setting.

According to some embodiments, the system may comprise a procedure compliance assessment module for comparing one or more of the scene related features detected and reported by the scene evaluation module to a list of expected actions or equipment usages associated with the procedure being performed in the treatment setting, and registering divergences between one or more of the detected scene features and, one or more of the actions or equipment usages associated with the procedure being performed in the treatment setting.

According to some embodiments, the system may comprise a procedure assistance module for providing procedure related action recommendations or instructions from within the list of expected actions or equipment usages, wherein one or more action recommendations or instructions are provided—upon the procedure compliance assessment module finding a divergence between one or more of the detected scene features and, one or more of the actions or equipment usages associated with the procedure being performed in the treatment setting, compared thereto.

According to some embodiments, the scene evaluation module may include an audio signature detection component and the procedure compliance assessment module may correlate detected sounds within the treatment setting with a certain step of the procedure associated with specific actions or specific medical equipment usage.

According to some embodiments, the scene evaluation module includes a video recognition component and the procedure compliance assessment module may correlate detected medical staff members participating in the procedure, and their orientation within the treatment setting, with a certain step of the procedure associated with specific actions or specific medical equipment usage.

According to some embodiments, the procedure assistance module may include an artificial intelligence module for shepherding medical staff through the medical procedure, by selecting the procedure related action recommendations or instructions to be provided and the order by which to provide them.

According to some embodiments, the artificial intelligence module may be a deep learning neural network model trained by supervised-learning, wherein the training data for the model may include sets of audio, video or medical-device procedure setting inputs and their corresponding, verified, action recommendations or instructions outputs.

According to some embodiments, the procedure assistance module may include a communication module for relaying the procedure related action recommendations or instructions along with the location of the medical procedure setting within a medical facility. And the system may further comprise a medical equipment positioning and navigation module for: monitoring the position of one or more autonomous mobile medical components within the medical facility; receiving, from the communication module, a medical procedure recommendation or instruction associated with at least some of the one or more autonomous mobile medical components; referencing a map of the medical facility and calculating navigation routes, to the location of the medical procedure setting, for the autonomous mobile medical components associated with the procedure recommendation or instruction, based on their current location; selecting the fastest route from within the calculated navigation routes; and/or communicating the fastest route navigation instructions to the autonomous mobile medical component associated therewith.

According to some embodiments, the procedure assistance module may include a communication module for relaying the procedure related action recommendations or instructions, along with a medical tool or item associated therewith. And the system may further comprise a medical tools or items storage component, the component including items or tools storage place indicators and, is adapted to receive the relayed procedure related action recommendations or instructions and upon receipt to indicate the storage place, within it, of the item or tool, relayed along with the received action recommendations or instructions.

According to some embodiments of the present invention, a medical procedure tracking and assistance method may include: acquiring video, audio or medical device feeds from a medical treatment setting; detecting scene related features in the video, audio or medical device feeds from the medical treatment setting; comparing one or more of the scene related features detected to a list of expected actions or equipment usages associated with the procedure being performed in the treatment setting; and/or registering divergences between one or more of the detected scene features and, one or more of the actions or equipment usages associated with the procedure being performed in the treatment setting.

According to some embodiments, the method may further include, providing procedure related action recommendations or instructions from within the list of expected actions or equipment usages, wherein one or more action recommendations or instructions are provided—upon finding a divergence between one or more of the detected scene features and, one or more of the actions or equipment usages associated with the procedure being performed in the treatment setting, compared thereto.

According to some embodiments, the method may further include, correlating detected sounds within the treatment setting with a certain step of the procedure associated with specific actions or specific medical equipment usage.

According to some embodiments, the method may further include, correlating detected medical staff members participating in the procedure, and their orientation within the treatment setting, with a certain step of the procedure associated with specific actions or specific medical equipment usage.

According to some embodiments, the method may further include, training a deep learning neural network model with training data including sets of audio, video or medical-device procedure setting inputs and their corresponding, verified, action recommendations or instructions outputs; and shepherding medical staff through the medical procedure, by selecting the procedure related action recommendations or instructions to be provided and the order by which to provide them, based on outputs from the deep learning neural network model.

According to some embodiments, the method may further include: relaying the procedure related action recommendations or instructions along with the location of the medical procedure setting within a medical facility; monitoring the position of one or more autonomous mobile medical components within the medical facility; receiving a medical procedure recommendation or instruction associated with at least some of the one or more autonomous mobile medical components; referencing a map of the medical facility and calculating navigation routes, to the location of the medical procedure setting, for the autonomous mobile medical components associated with the procedure recommendation or instruction, based on their current location; selecting the fastest route from within the calculated navigation routes; and/or communicating the fastest route navigation instructions to the autonomous mobile medical component associated therewith.

According to some embodiments, the method may further include, relaying the procedure related action recommendations or instructions, along with a medical tool or item associated therewith; and indicating the storage place, of the item or tool, relayed along with the received action recommendations or instructions.

The subject matter described above is provided by way of illustration only and should not be constructed as limiting. While certain features of the invention have been illustrated and described herein, many modifications, substitutions, changes, and equivalents will now occur to those skilled in the art. It is, therefore, to be understood that the appended claims are intended to cover all such modifications and changes as fall within the true spirit of the invention.

The invention claimed is:

1. A medical procedure tracking and assistance system, said system comprising:
   one or more video cameras, one or more acoustic sensors or one or more medical device interfaces for acquiring video, audio or medical device feeds from a medical treatment setting; a scene evaluation module for detecting scene related features in the video, audio or medical device feeds from the medical treatment setting;
   a procedure compliance assessment module for comparing one or more of the scene related features detected and reported by said scene evaluation module to a list of expected actions or equipment usages associated with the procedure being performed in the treatment setting, and registering divergences between one or more of the detected scene features and, one or more of the actions or equipment usages associated with the procedure being performed in the treatment setting;
   a procedure assistance module for providing procedure related action recommendations or instructions from within the list of expected actions or equipment usages, wherein one or more action recommendations or instructions are provided upon said procedure compliance assessment module finding a divergence between one or more of the detected scene features and one or more of the actions or equipment usages associated with the procedure being performed,
   and wherein said procedure assistance module includes communication functionality for relaying the procedure related action recommendations or instructions, along with a medical tool or item associated therewith; and
   a medical tools or items storage component including items or tools storage place indicators and adapted to receive the relayed procedure related action recommendations or instructions and upon receipt to indicate the storage place, within it, of the item or tool, relayed along with the received action recommendations or instructions.

2. The system according to claim 1, wherein said scene evaluation module includes an audio signature detection component and said procedure compliance assessment module correlates detected sounds within the treatment setting with a certain step of the procedure associated with specific actions or specific medical equipment usage.

3. The system according to claim 1, wherein said scene evaluation module includes a video recognition component and said procedure compliance assessment module correlates detected medical staff members participating in the procedure, and their orientation within the treatment setting, with a certain step of the procedure associated with specific actions or specific medical equipment usage.

4. The system according to claim 1, wherein said procedure assistance module includes an artificial intelligence module for shepherding medical staff through the medical procedure, by selecting the procedure related action recommendations or instructions to be provided and the order by which to provide them.

5. The system according to claim 4, wherein said artificial intelligence module is a deep learning neural network model trained by supervised-learning, wherein the training data for the model includes sets of audio, video or medical-device procedure setting inputs and their corresponding, verified, action recommendations or instructions outputs.

6. The system according to claim 1, wherein said procedure assistance module further includes a communication module for relaying the procedure related action recommendations or instructions along with the location of the medical procedure setting within a medical facility; and wherein said system further comprises a medical equipment positioning and navigation module for: (a) monitoring the position of one or more autonomous mobile medical components within the medical facility; (b) receiving, from said communication module, a medical procedure recommendation or instruction associated with at least some of the one or more autonomous mobile medical components; (c) referencing a map of the medical facility and calculating navigation routes, to the location of the medical procedure setting, for the autonomous mobile medical components associated with the procedure recommendation or instruction, based on their current location; (d) selecting the fastest route from within the calculated navigation routes; (e) communicating the fastest route navigation instructions to the autonomous mobile medical component associated therewith.

7. A medical procedure tracking and assistance method, said method including:
  acquiring video, audio or medical device feeds from a medical treatment setting; detecting scene related features in the video, audio or medical device feeds from the medical treatment setting; comparing one or more of the scene related features detected to a list of expected actions or equipment usages associated with the procedure being performed in the treatment setting;
  registering divergences between one or more of the detected scene features and one or more of the actions or equipment usages associated with the procedure being performed in the treatment setting; and
  providing procedure related action recommendations or instructions from within the list of expected actions or equipment usages, wherein one or more action recommendations or instructions are provided upon finding a divergence between one or more of the detected scene features and one or more of the actions or equipment usages associated with the procedure being performed, and relaying the procedure related action recommendations or instructions, along with a medical tool or item associated therewith to a medical tools or items storage component including items or tools storage place indicators and adapted to receive the relayed procedure related action recommendations or instructions and upon receipt to indicate the storage place, within it, of the item or tool, relayed along with the received action recommendations or instructions.

8. The method according to claim 7, further including, correlating detected sounds within the treatment setting with a certain step of the procedure associated with specific actions or specific medical equipment usage.

9. The method according to claim 7, further including, correlating detected medical staff members participating in the procedure, and their orientation within the treatment setting, with a certain step of the procedure associated with specific actions or specific medical equipment usage.

10. The method according to claim 7, further including: training a deep learning neural network model with training data including sets of audio, video or medical-device procedure setting inputs and their corresponding, verified, action recommendations or instructions outputs; and shepherding medical staff through the medical procedure, by selecting the procedure related action recommendations or instructions to be provided and the order by which to provide them, based on outputs from the deep learning neural network model.

11. The method according to claim 7, further including: relaying the procedure related action recommendations or instructions along with the location of the medical procedure setting within a medical facility; monitoring the position of one or more autonomous mobile medical components within the medical facility; receiving a medical procedure recommendation or instruction associated with at least some of the one or more autonomous mobile medical components; referencing a map of the medical facility and calculating navigation routes, to the location of the medical procedure setting, for the autonomous mobile medical components associated with the procedure recommendation or instruction, based on their current location; selecting the fastest route from within the calculated navigation routes; and communicating the fastest route navigation instructions to the autonomous mobile medical component associated therewith.

* * * * *